(12) United States Patent
Tu

(10) Patent No.: US 12,025,592 B1
(45) Date of Patent: Jul. 2, 2024

(54) METHOD FOR PURIFYING EXOSOMES FROM A CELL CULTURE MEDIUM

(71) Applicant: Lan Ngoc Ly Tu, Ho Chi Minh (VN)

(72) Inventor: Lan Ngoc Ly Tu, Ho Chi Minh (VN)

(73) Assignee: NEXCALIBUR THERAPEUTICS, CORP., Lewes, DE (US)

( * ) Notice: Subject to any disclaimer, the term of this patent is extended or adjusted under 35 U.S.C. 154(b) by 0 days.

(21) Appl. No.: 18/452,589

(22) Filed: Aug. 21, 2023

(51) Int. Cl.
| | | |
|---|---|---|
| *G01N 30/02* | (2006.01) | |
| *B01D 37/04* | (2006.01) | |
| *B01D 43/00* | (2006.01) | |
| *B01D 61/14* | (2006.01) | |
| *C12N 5/073* | (2010.01) | |
| *C12N 9/16* | (2006.01) | |

(52) U.S. Cl.
CPC ........... *G01N 30/02* (2013.01); *B01D 37/043* (2013.01); *B01D 37/046* (2013.01); *B01D 43/00* (2013.01); *B01D 61/145* (2013.01); *C12N 5/0603* (2013.01); *C12N 9/16* (2013.01); *C12Y 301/30002* (2013.01)

(58) Field of Classification Search
CPC .... G01N 30/02; B01D 37/043; B01D 37/046; B01D 43/00; B01D 61/145; C12N 5/0603; C12N 9/16; C12Y 301/30002
See application file for complete search history.

(56) References Cited

FOREIGN PATENT DOCUMENTS

| | | | | |
|---|---|---|---|---|
| WO | WO-2021130417 A1 | * | 7/2021 | ............. C07K 14/00 |
| WO | WO-2022182782 A1 | * | 9/2022 | |

OTHER PUBLICATIONS

Corso, G., et al., "Reproducible and scalable purification of extracellular vesicles using combined bind-elute and size exclusion chromatography", Scientific Reports, 7: 11561. (Year: 2017).*
GE Healthcare Bio-Sciences AB, "HiScreen CaptoCore 700 HiTrap CaptoCore 700, 1 mL". Instructions 28-9958-81 AF. April. (Year: 2014).*
Genetic Engineering and Biotechnology News, "Optimizing tangential flow filtration". Oct. 17. (Year: 2022).*
Gorgens, A., et al., "Identification of storage conditions stabilizing extracellular vesicles preparations", J Extracell Vesicles, 11, e12238. (Year: 2022).*
Merck Millipore, "Benzonase endonuclease". July. (Year: 2023).*
Tran et al., "Dual-targeting exosomes for improved drug delivery in breast cancer", Nanomedicine, 18(7), 599-611. (Year: 2023).*
Thery, C., et al., "Isolation and characterization of exosomes from cell culture supernatants and biological fluids", Current protocols in cell biology, 3.22.1-3.22.29. (Year: 2006).*

* cited by examiner

*Primary Examiner* — Benjamin L Lebron

(57) ABSTRACT

A method for purifying exosomes from a cell culture medium comprising combining at least three (03) treating stages of a sample containing exosomes in the following specific order: (A) filtering the sample containing exosomes by tangential flow filtration (TFF) to obtain a TFF-filtered sample; (B) centrifuging the TFF-filtered sample by sucrose cushion centrifugation (SCC) to obtain a SCC-centrifuged sample; and (C) purifying the SCC-centrifuged sample by bind-elute size exclusion chromatography (BE-SEC) to obtain a purified exosomes. The present invention provides a comprehensive and efficient approach for purifying exosomes from a cell culture medium, facilitating using exosomes in various biomedical applications.

3 Claims, 19 Drawing Sheets

METHOD FOR PURIFYING EXOSOMES FROM A CELL CULTURE MEDIUM

FIELD OF THE INVENTION

The present invention relates to an exosome purification method. More specifically, the present invention relates to a method for purifying exosomes from a cell culture medium, aiming to achieve high levels of purity and enable mass production.

BACKGROUND ART

Exosomes, small extracellular vesicles that play a crucial role in intercellular communication, offer significant potential as biomarkers and drug-delivery vehicles. Their unique content profile, specific to each cell type, and their ability to be efficiently taken up by target cells make them attractive candidates in various biomedical applications. However, isolating and purifying exosomes poses challenges due to their small size (around 100 nm) and heterogeneity, making it necessary to distinguish them from other extracellular vesicles like microvesicles, lipoproteins, and cellular debris.

Many methods are available for exosome isolation, each with advantages and limitations. Ultracentrifugation, ultra-filtration, ion exchange techniques, affinity techniques, and size-exclusion chromatography are commonly employed. Ultracentrifugation involves high-speed centrifugation to pellet the exosomes based on density, while ultrafiltration relies on size-based separation using porous membranes. Ion-exchange techniques utilize the charged properties of exosomes to bind them to charged surfaces or resins selectively. Affinity techniques exploit specific interactions between exosomes and antibodies or ligands attached to solid supports. Size-exclusion chromatography separates exosomes based on their size using a porous matrix.

Each isolation method has its advantages and challenges, and the choice of method depends on the specific requirements of the study or application. Further advancements in exosome isolation techniques are necessary to improve yield, purity, and scalability, ultimately enhancing their utility in research and clinical settings.

According to U.S. Pat. No. 6,812,023 B1 refers to a method for preparing membrane vesicles, comprising: (a) obtaining a population of antigen-presenting cells; (b) sensitizing the antigen-presenting cells to one or several antigens; (c) culturing the population of antigen-presenting cells under conditions allowing the release of membrane vesicles by antigen-presenting cells; (d) a clarification of the culture supernatant; (e) a concentration of the clarified supernatant; (f) a diafiltration of the concentrated supernatant; (g) the isolation of the membrane vesicles using density cushion centrifugation in a cushion buffer; (h) diafiltration to exchange the cushion buffer with a formulation buffer; and (i) a sterile filtration of the vesicle membranes obtained in (h).

According to patent application No. US 2022/0364051 A1 refers to a method for isolating plant exosomes, comprising: (a) performing centrifugation; and (b) performing tangential-flow filtration (TFF). Wherein the centrifugation comprises ultracentrifugation; the tangential-flow filtration is one or more selected from the group consisting of hollow fiber TFF and membrane TFF; the tangential-flow filtration uses a TFF filter with a molecular weight cut-off (MWCO) of 100,000 Da to 500,000 Da.

According to patent application No. US 2022/0364051 A1 refers to an exosome production method consisting of: (i) ultra-filtering a biological sample containing exosomes; and (ii) subjecting the resulting sample from step (i) to anion exchange column chromatography. In this method, the ultra-filtration process employs a tangential flow filtration machine/device with a filter pore size of approximately 0.06 μm to 0.07 μm and a nominal MWCO of around 750 kDa. The anion exchange column chromatography employs a weakly basic anion exchanger with selectivity based on hydrophobic interaction and hydrophobic binding formation, incorporating a phenyl group, an amide bond, and a carboxyl group. The anion exchange column chromatography is performed in the presence of 0.15 M to 0.8 M NaCl or KCl, under neutral pH conditions ranging from 7.2 to 7.7.

The above inventions meet the specific purposes and requirements of a technical solution. However, there is still a need for an improved method to generate exosomes with high purity and efficiency.

Therefore, it is necessary to create a standard workflow for exosome purification that can be effectively upscaled.

Furthermore, it is necessary to create a method for purifying exosomes from a cell culture medium comprising: (i) preparing the sample containing exosomes; (ii) filtering the sample containing exosomes by tangential flow filtration (TFF) to obtain a TFF-filtered sample; (iii) centrifuging the TFF-filtered sample by sucrose cushion centrifugation (SCC) to obtain a SCC-centrifuged sample; (iv) purifying the SCC-centrifuged sample by bind-elute size exclusion chromatography to obtain a purified exosomes; (v) centrifuging the purified exosomes to obtain a centrifuged-purified exosomes; and (vi) preserving the centrifuged-purified exosomes in a storage buffer.

Finally, what is needed to provide a method for purifying exosomes from a cell culture medium that offers simplified steps, optimized technical specifications, and the potential for industrial-scale application.

This invention provides solutions to achieve the above goals.

SUMMARY OF THE INVENTION

Accordingly, an objective of the present invention is to provide a method for purifying exosomes from a cell culture medium comprising combining at least three (03) treating stages of a sample containing exosomes in the following specific order: (A) filtering the sample containing exosomes by tangential flow filtration (TFF) to obtain a TFF-filtered sample; (B) centrifuging the TFF-filtered sample by sucrose cushion centrifugation (SCC) to obtain a SCC-centrifuged sample; and (C) purifying the SCC-centrifuged sample by bind-elute size exclusion chromatography (BE-SEC) to obtain a purified exosomes;

wherein (A) filtering the sample containing exosomes by tangential flow filtration (TFF) by the tangential flow filtration machine/device with the following set parameters: a pore size of 300 kDa, a feed flow rate of 25 mL/minute, and a transmembrane pressure of 0.7 bar-1.0 bar, comprising:
  filtering the sample containing exosomes until the volume of the sample containing exosomes is reduced from 10 to 20 times to obtain a first filtered sample containing exosomes; and
  diafiltrating the first filtered sample containing exosomes two (02) times to obtain the TFF-filtered sample;

wherein (B) centrifuging the TFF-filtered sample by sucrose cushion centrifugation (SCC) by the centrifugation machine/device, comprising:

centrifuging the TFF-filtered sample in a 30% sucrose solution to obtain a sucrose fraction containing exosomes;

mixing the Phosphate Buffered Saline (PBS) buffer with the sucrose fraction containing exosome to obtain a foundation solution; and centrifuging the foundation solution, removing the liquid phase to obtain the SCC-centrifuged sample;

wherein (C) purifying the SCC-centrifuged sample by bind-elute size exclusion chromatography (BE-SEC) by the size exclusion chromatography machine/device with a chromatography column containing 1-20 mL resin beads, and the recovery rate is set at 0.5-1.5 mL/minute.

Another objective of the present invention is to provide a process for purifying exosomes from a cell culture medium comprising:

(i) preparing the sample containing exosomes in a specific order from (a) to (e) comprising:
  (a) centrifuging the cell culture medium containing exosomes by the centrifugation machine/device at 300×g for 5 minutes to obtain the first supernatant in the upper phase;
  (b) centrifuging the first supernatant at step (a) by the centrifugation machine/device at 3,000-10,000×g for 30 minutes to obtain the second supernatant in the upper phase;
  (c) filtering the second supernatant at step (b) by a filter membrane with a pore size of 0.22 μm to obtain the filtered solution containing exosomes;
  (d) treating the filtered solution containing exosomes at step (c) by enzyme Benzonase© at a concentration ranging from 0.2 U/mL to 1 U/mL for 2 hours to obtain the filtrate containing enzyme-treated exosomes; and
  (e) mixing the buffer/water-based balanced salt solution to the filtrate containing enzyme-treated exosomes at step (d) at a ratio of (1-3) parts of the buffer/water-based balanced salt solution to 1 part of filtrate containing enzyme-treated exosomes to obtain the sample containing exosomes;

(ii) filtering the sample containing exosomes at step (i) by tangential flow filtration (TFF), comprising:
  (a') filtering the sample containing exosomes until the volume of the sample containing exosomes is reduced from 10 to 20 times to obtain the first filtered sample containing exosomes; and
  (b') diafiltrating the first filtered sample containing exosomes two (02) times, comprising:
    a first time: mixing the buffer/water-based balanced salt solution to the first filtered sample containing exosomes at a ratio of 1:1 to obtain a first temporary mixture, then filtering the first temporary mixture until the volume of the first temporary mixture is reduced by 50 percent to obtain a second filtered sample containing exosomes; and
    a second time: mixing the buffer/water-based balanced salt solution to the second filtered sample containing exosomes at a ratio of 1:1 to obtain a third temporary mixture, then filtering the third temporary mixture until the volume of the third temporary mixture is reduced by 50 percent to obtain the TFF-filtered sample;

(iii) centrifuging the TFF-filtered sample at step (ii) by sucrose cushion centrifugation (SCC) in a specific order from (a") to (c") comprising:
  (a") centrifuging the centrifuge tube containing 8 parts of the TFF-filtered sample at stage (A) and 2 parts of 30% sucrose solution at 100,000-130,000×g for at least 3 hours at 4° C.; then removing 6-7 parts of the solution from the upper phase of the centrifuge tube, collecting the sucrose fraction containing exosomes in the remaining 3-4 parts at the bottom of the centrifuge tube;
  (b") mixing 6-7 parts the Phosphate Buffered Saline (PBS) buffer with the sucrose fraction containing exosomes to obtain the foundation solution; and
  (c") centrifuging the foundation solution at 100,000-130,000×g for 3 hours at 4° C., removing the liquid phase to obtain the SCC-centrifuged sample;

(iv) purifying the SCC-centrifuged sample at step (iii) by bind-elute size exclusion chromatography (BE-SEC) by the size exclusion chromatography machine/device in a specific order from (a''') to (b''') comprising:
  (a''') mixing the Phosphate Buffered Saline (PBS) buffer into the SCC-centrifuged sample at stage (B) to obtain a suspension containing exosomes; and
  (b''') loading the suspension containing exosomes into the chromatography column containing 1-20 mL of resin beads at a rate of 0.5-1.5 mL/minute, and purifying to obtain the purified exosomes, comprising the following three steps:
    step 1: recovering a first fraction based on the UV 280 nm peak signal at a recovery rate of 0.5-1.5 mL/minute;
    step 2: further recovering a second fraction containing 10 mL after the UV 280 nm peak signal at a recovery rate of 0.5-1.5 mL/minute; and
    step 3: creating the purified exosomes by mixing the first fraction based on the UV 280 nm peak signal and the second fraction containing 10 mL after the UV 280 nm peak signal;

(v) centrifuging the purified exosomes at step (iv) by the centrifugation machine/device using a fixed-angle rotor at 100,000-130,000×g for 3 hours at 4° C., removing the supernatant to obtain a centrifuged-purified exosomes; and (vi) preserving the centrifuged-purified exosomes at step (v) in a storage buffer; wherein the storage buffer containing a human serum albumin component having 0.05%-0.3% by weight of the storage buffer.

Finally, the purpose of the present invention is to provide an efficient method/process for purifying exosomes from a cell culture medium, ensuring high recovery efficiency and purity. The resulting exosomes meet the required standards for size, intact shape, and safety characteristics, making them suitable for various applications in biotechnology and biomedical research.

These and other advantages of the present invention will no doubt become obvious to those of ordinary skill in the art after having read the following detailed description of the preferred embodiments, which are illustrated in the various drawing Figures.

BRIEF DESCRIPTION OF THE DRAWING

The accompanying drawings, which are incorporated in and form a part of this specification, illustrate embodiments of the invention and, together with the description, serve to explain the principles of the invention.

DETAILED DESCRIPTION OF THE INVENTION

Reference will now be made in detail to the preferred embodiments of the invention, examples of which are illustrated in the accompanying drawings. While the invention will be described in conjunction with the preferred embodiments, it will be understood that they are not intended to limit the invention to these embodiments. On the contrary, the invention is intended to cover alternatives, modifications, and equivalents, which may be included within the spirit and scope of the invention as defined by the appended claims. Furthermore, in the following detailed description of the present invention, numerous specific details are set forth in order to provide a thorough understanding of the present invention. However, it will be obvious to one of ordinary skill in the art that the present invention may be practiced without these specific details. In other instances, well-known methods, procedures, components, and circuits have not been described in detail so as not to unnecessarily obscure aspects of the present invention.

Please note that filtration machines/devices, centrifugation machines/devices, tangential flow filtration machines/devices, chromatography machines/devices, etc., and other similar machines/devices are well-known in the fields of biochemistry, biomedical sciences, and biotechnology. Therefore, detailed descriptions and operating principles of these machines/devices are not provided to avoid obscuring unnecessary aspects of the invention.

It should be noted that the term "buffer/water-based balanced salt solution" is used in this invention, it is selected from one of the buffer/water-based balanced salt solution types including Phosphate Buffered Saline (PBS), Dulbecco's Phosphate Buffered Saline (DPBS), HEPES Buffered Saline (HBS), and Hanks' Balanced Salt Solution (HBSS).

Figure 1:
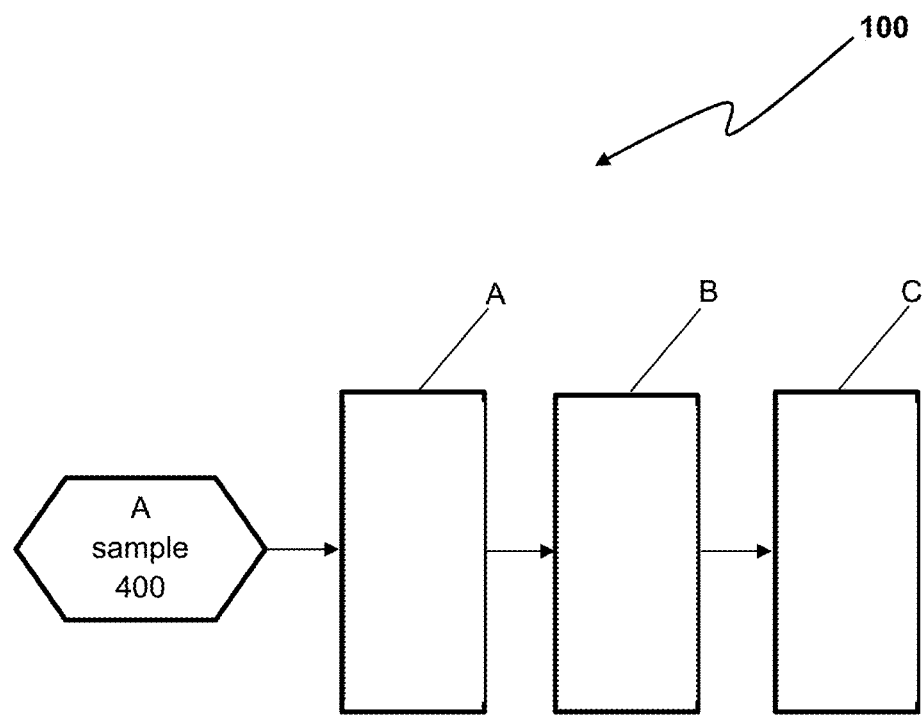
FIG. 1 is a block diagram illustrating the first principle of a method for purifying exosomes from cell culture medium 100 ("method 100") in accordance with an exemplary embodiment of the present invention.

Now referring to FIG. 1, is a block diagram illustrating the first principle of a method for purifying exosomes from cell culture medium 100 ("method 100") according to the embodiment of the present invention. A sample containing exosomes 400 ("sample 400") purified by method 100 which consists of at least three (03) treating stages in a specific order including: a stage A, a stage B, and a stage C; wherein the stage A: filtering the sample 400 by tangential flow filtration (TFF) by the tangential flow filtration machine/device with the following set parameters: a pore size of 300 kDa, a feed flow rate of 25 mL/minute, and a transmembrane pressure of 0.7 bar-1.0 bar to obtain a TFF-filtered sample;

the stage B: centrifuging the TFF-filtered sample at stage A by sucrose cushion centrifugation (SCC) to obtain a SCC-centrifuged sample, comprising:
  centrifuging the TFF-filtered sample in a 30% sucrose solution to obtain a sucrose fraction containing exosomes;
  mixing the Phosphate Buffered Saline (PBS) buffer with the sucrose fraction containing exosome to obtain a foundation solution; and
  centrifuging the foundation solution, removing the liquid phase to obtain the SCC-centrifuged sample;

the stage C: purifying the SCC-centrifuged sample at stage B by bind-elute size exclusion chromatography (BE-SEC) to obtain a purified exosomes; wherein the stage C using the size exclusion chromatography machine/device with a chromatography column containing 1-20 mL resin beads, and the recovery rate is set at 0.5-1.5 mL/minute.

According to the embodiment of the invention, stage A is the filtration stage of the sample 400, which includes one (01) time of tangential flow filtration (TFF) and two (02) times of diafiltration, comprising:
- creating a first filtered sample containing exosomes by filtering the sample 400 until the volume of the sample 400 is reduced from 10 to 20 times; and
- creating the TFF-filtered sample by diafiltrating the first filtered sample containing exosomes two (02) times, comprising:
  - a first time: mixing the buffer/water-based balanced salt solution to the first filtered sample containing exosomes at a ratio of 1:1 to obtain a first temporary mixture, then filtering the first temporary mixture until the volume of the first temporary mixture is reduced by 50 percent to obtain a second filtered sample containing exosomes; and
  - a second time: mixing the buffer/water-based balanced salt solution to the second filtered sample containing exosomes at a ratio of 1:1 to obtain a third temporary mixture, then filtering the third temporary mixture until the volume of the third temporary mixture is reduced by 50 percent to obtain the TFF-filtered sample.

According to the embodiment of the invention, the stage B is the centrifugation stage of the TFF-filtered sample at stage A by sucrose cushion centrifugation (SCC) by the centrifugation machine/device, comprising:
- centrifuging the centrifuge tube containing 8 parts of the TFF-filtered sample at stage (A) and 2 parts of 30% sucrose solution at 100,000-130,000×g for at least 3 hours at 4° C.; then removing 6-7 parts of the solution from the upper phase of the centrifuge tube, collecting the sucrose fraction containing exosomes in the remaining 3-4 parts at the bottom of the centrifuge tube;
- mixing 6-7 parts the Phosphate Buffered Saline (PBS) buffer with the sucrose fraction containing exosomes to obtain the foundation solution; and
- centrifuging the foundation solution at 100,000-130,000×g for 3 hours at 4° C., removing the liquid phase to obtain the SCC-centrifuged sample.

According to the preferred embodiment of the present invention, at stage B, centrifuging the TFF-filtered sample by sucrose cushion centrifugation (SCC) to obtain the SCC-centrifuged sample by the centrifugation machine/device using a fixed-angle rotor.

According to the preferred embodiment of the present invention, at stage B, the TFF-filtered sample is centrifuged by sucrose cushion centrifugation for a maximum time period of 16 hours.

According to the embodiment of the invention, the stage C is the purification stage of the SCC-centrifuged sample at stage B in a specific order comprising:
- mixing the Phosphate Buffered Saline (PBS) buffer into the SCC-centrifuged sample at stage (B) to obtain a suspension containing exosomes; and
- loading the suspension containing exosomes into the chromatography column containing 1-20 mL of resin beads at a rate of 0.5-1.5 mL/minute, and purifying to obtain the purified exosomes, comprising the following three steps:
  - step 1: recovering a first fraction based on the UV 280 nm peak signal at a recovery rate of 0.5-1.5 mL/minute;
  - step 2: further recovering a second fraction containing 10 mL after the UV 280 nm peak signal at a recovery rate of 0.5-1.5 mL/minute; and
  - step 3: creating the purified exosomes by mixing the first fraction based on the UV 280 nm peak signal and the second fraction containing 10 mL after the UV 280 nm peak signal.

According to the preferred embodiment of the present invention, at stage (C), purifying the SCC-centrifuged sample by bind-elute size exclusion chromatography (BE-SEC) by the size exclusion chromatography machine/device with the chromatography column containing 5 mL resin beads.

The results demonstrate that the method of purifying exosomes by combining at least three (03) treating stages of the sample 400, including stage A, stage B, and stage C, achieves better efficiency compared to methods with a single treating stage or a combination of two treating stages. This is demonstrated based on the evaluation criteria, including CD81 marker testing, purity, particle yield, and DNA contaminant ratio in the experiment assessing the effectiveness of different exosome purification methods presented in Table 1.

TABLE 1

Experimental results of CD81 marker testing, purity, particle yield, and DNA contamination ratio of the obtained exosomes in different methods of exosome purification

| Experimental conditions | CD81 marker testing | Purity (fold change) | Particle yield (%) | DNA contaminant ratio (%) |
| --- | --- | --- | --- | --- |
| TFF | + | 0.1 | 9.5 | 100 |
| TFF-UC30 | + | 0.4 | 38.0 | 28 |
| TFF-FPLC | + | 0.1 | 1.5 | 37 |
| TFF-UC30-FPLC | + | 1.0 | 100 | 21.5 | in which:
(+) means that the CD81 marker testing yields a positive result;
TFF: the sample 400 is purified using a method that includes the filtration stage by tangential flow filtration;
TFF-UC30: the sample 400 is purified using a method that combines the filtration stage by tangential flow filtration and the centrifugation stage by sucrose cushion centrifugation;
TFF-FPLC: the sample 400 is purified using a method that combines the filtration stage by tangential flow filtration and the purification stage by bind-elute size exclusion chromatography.
TFF-UC30-FPLC: the sample 400 is purified using a method that combines three (03) treating stages in the following specific order: the filtration stage by tangential flow filtration, the centrifugation stage by sucrose cushion centrifugation, and the purification stage by bind-elute size exclusion chromatography.

Figure 2:
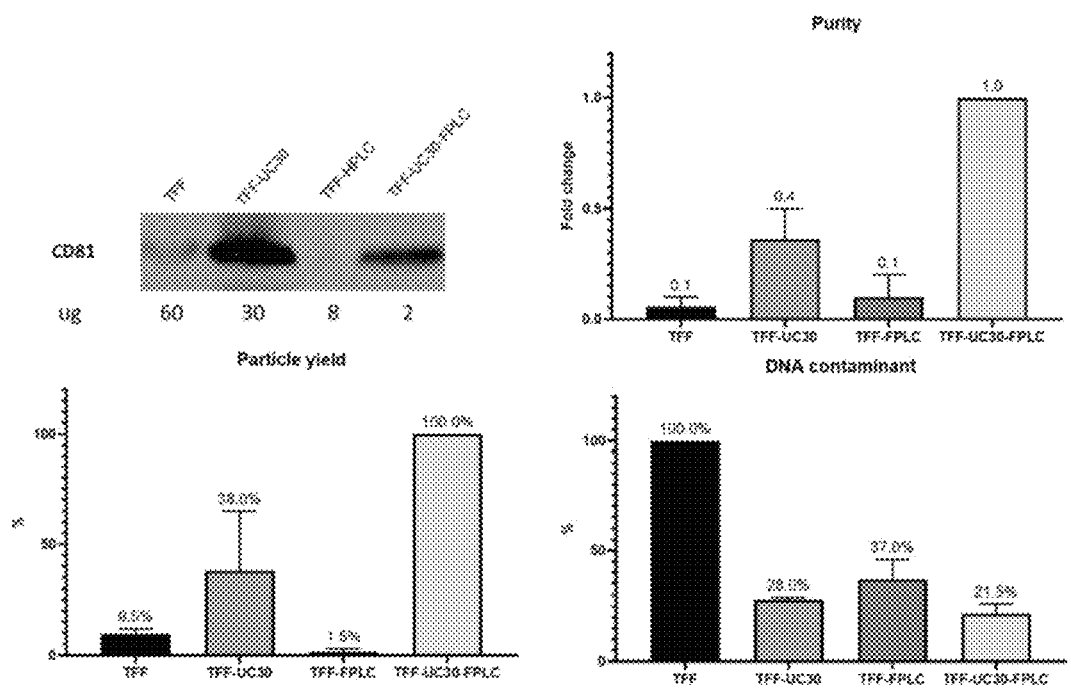
FIG. 2 is a chart illustrating the results of the experiment assessing the effectiveness of the method 100 according to the embodiment of the invention.

Based on Table 1, the results of CD81 marker testing were positive for all four formulations, indicating the presence of exosomes in all of them. The evaluation of exosome purity revealed that the TFF-UC30-FPLC condition had the highest purity with a fold change of 1.0. The particle yield efficiency of exosomes decreased in the following order: TFF-UC30-FPLC, TFF-UC30, TFF, and TFF-FPLC, with corresponding ratios of 100%, 38%, 9.5%, and 1.5%, respectively. In terms of DNA contaminant ratio, the TFF condition had the highest ratio at 100%, while the TFF-UC30-FPLC condition had the lowest ratio at only 21.5% (referenced by FIG. 2).

Figure 3:
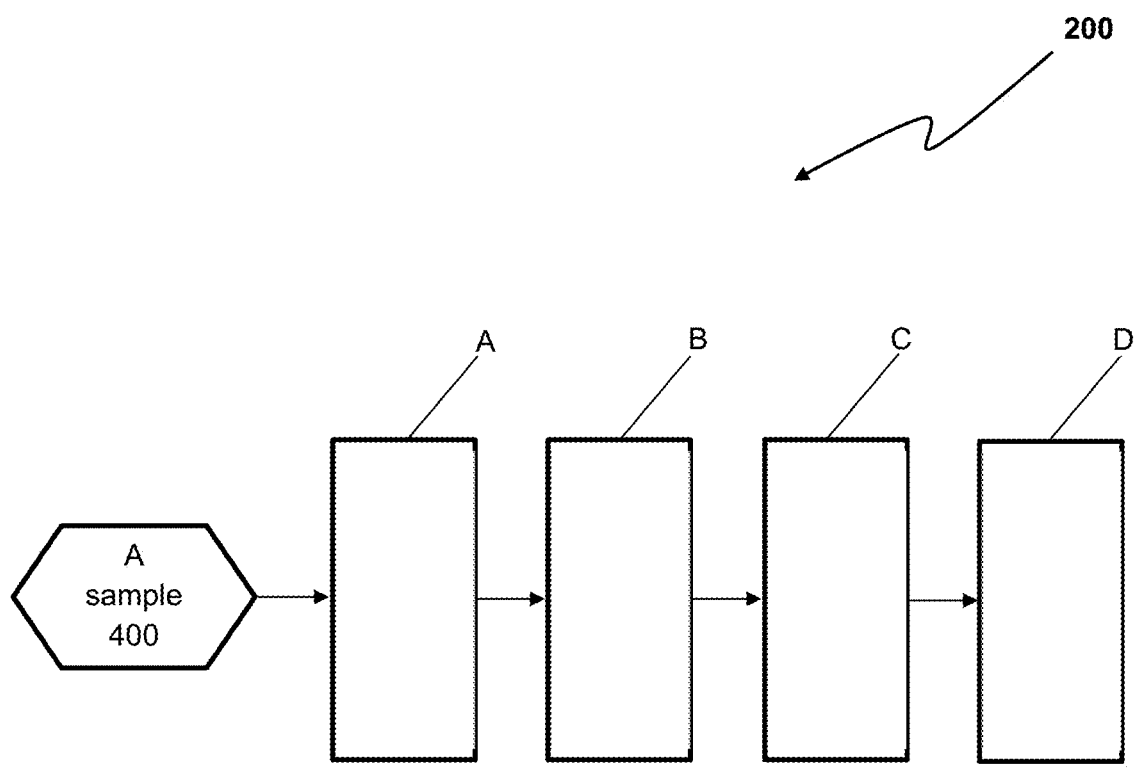
FIG. 3 is a block diagram illustrating the second principle of a method for purifying exosomes from cell culture medium 200 ("method 200") in accordance with an exemplary embodiment of the present invention.

Referring to FIG. 3 is a block diagram illustrating the second principle of a method for purifying exosomes from cell culture medium 200 ("method 200") according to the embodiment of the present invention. The method 200 is a variant of method 100 with the additional inclusion of the stage D. According to the embodiment of the invention, the sample 400 purified by method 200 which consists of four (04) treating stages in a specific order including: the stage A, the stage B, the stage C, and a stage D; wherein
- the stage A, the stage B, and the stage C, that have been described specification similarly to according the method 100 above;
- the stage D: centrifuging the purified exosomes at stage (C) by the centrifugation machine/device using a fixed-angle rotor at 100,000-130,000×g for 3 hours at 4° C. to remove the supernatant to obtain a centrifuged-purified exosomes.

Figure 4:
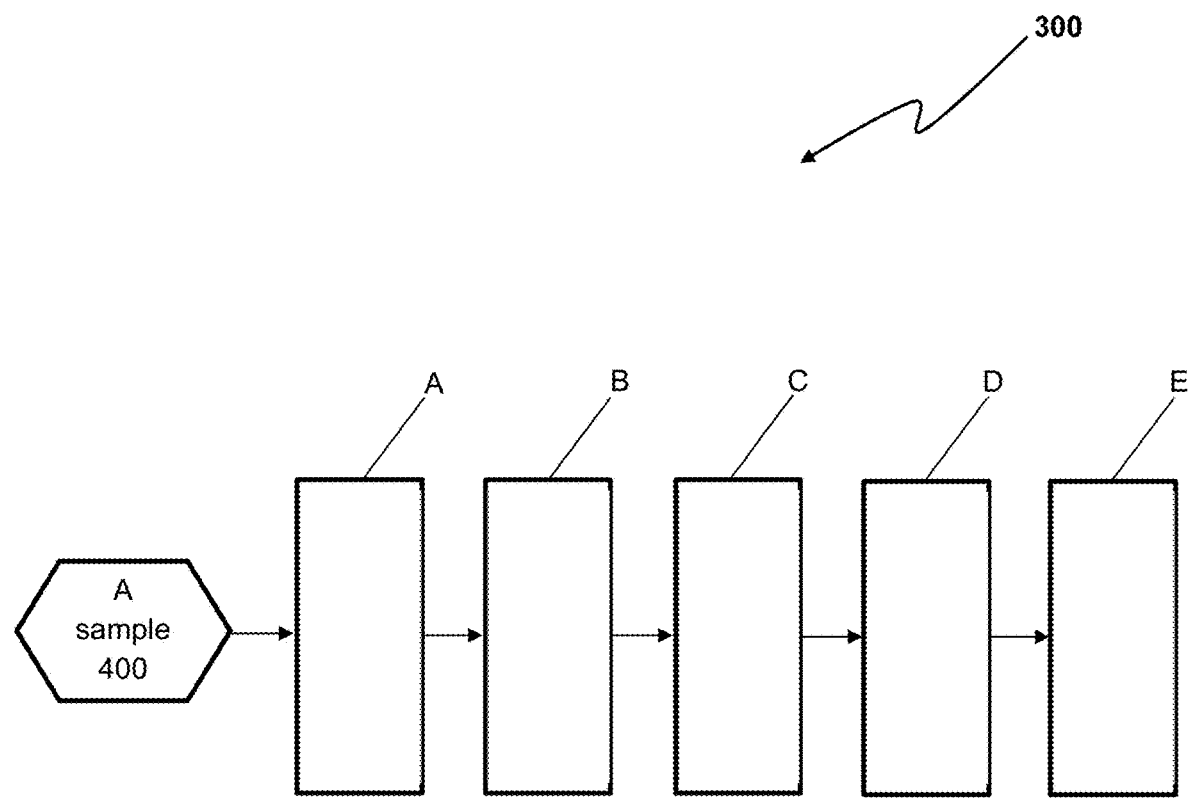
FIG. 4 is a block diagram illustrating the third principle of a method for purifying exosomes from cell culture medium 300 ("method 300") in accordance with an exemplary embodiment of the present invention.

Referring to FIG. 4 is a block diagram illustrating the third principle of a method for purifying exosomes from cell culture medium 300 ("method 300") according to the embodiment of the present invention. The method 300 is a variant of method 100 with the additional inclusion of the stage E. According to the embodiment of the invention, the sample 400 purified by method 300 which consists of five (05) treating stages in a specific order including: the stage A, the stage B, the stage C, the stage D, and a stage E; wherein
the stage A, the stage B, and the stage C, that have been described specification similarly to according the method 100 above;
the stage D has been described specification similarly to according the method 200 described above; and
the stage E: preserving the centrifuged-purified exosomes at stage (D) in a storage buffer.

In the embodiment of the present invention, the storage buffer contains human serum albumin component with a concentration ranging from 0.05% to 0.3% by weight of the storage buffer.

According to the preferred embodiment of the present invention, the storage buffer also containing chemical components consisting of an elemental sodium (Na) having 150-250 mmol/l, an elemental potassium (K) having 4 mmol/l, an elemental magnesium (Mg) having 1 mmol/l, an elemental calcium (Ca) having 2.5 mmol/l, an elemental chloride (Cl) having 130-230 mmol/l, an elemental acetate ($C_2H_3O$) having 24 mmol/l, and an elemental maleate ($C_4H_2O_4$) having 5 mmol/l.

In the embodiment of the present invention, the sample 400 purified by method 300 better than the sample 400 purified by method 200, and the sample 400 purified by method 200 better than the sample 400 purified by method 100; wherein a comparison factor is based on purity, particle yield, and DNA contaminant ratio of the sample 400 purified by the method from 100 to 300.

Figure 5:
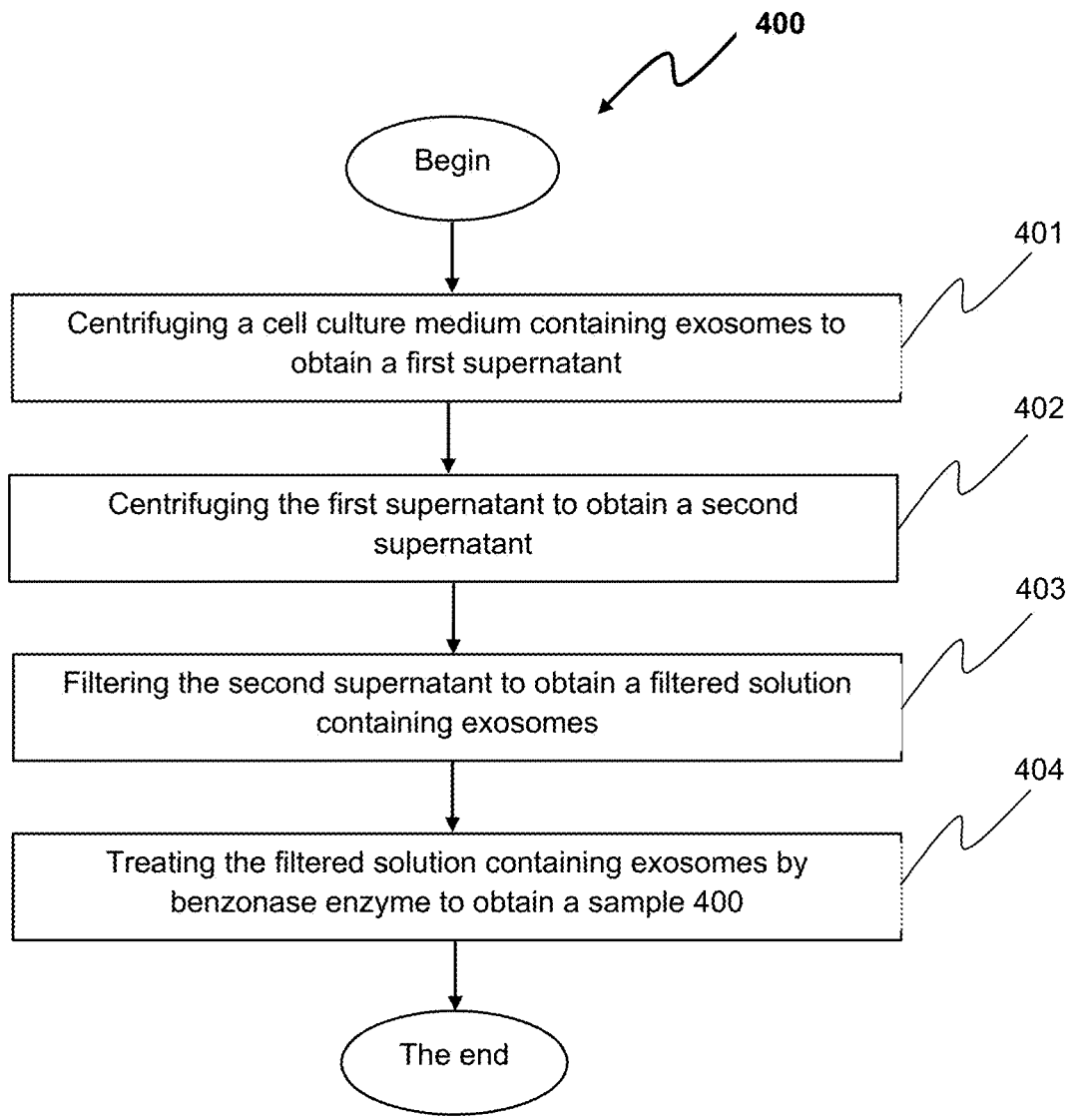
FIG. 5 is a flowchart illustrating a first process creating the sample 400 according to the embodiment of the invention.

According to the embodiment of the invention, the sample 400 mentioned in methods 100, 200, and 300, that is obtained from a first process 400 ("process 400") as referenced in FIG. 5. The process 400 begins with at step 401, which involves centrifuging a cell culture medium containing exosomes by the centrifugation machine/device at 300×g for 5 minutes to obtain a first supernatant in the upper phase.

According to the preferred embodiment of the present invention, the cell culture medium containing exosomes obtained by culturing cells selected from one of the cell types including mesenchymal stem cells (MSCs), neural stem cells (NSCs), human embryonic kidney 293 cells (HEK293), dendritic cells (DCs), cardiospherederived cell (CDCs), and chimeric antigen receptor-T cells (CAR-T).

According to the preferred embodiment of the present invention, the cell culture medium containing exosomes obtained by culturing human embryonic kidney 293 cells (HEK293).

At step 402, centrifuging the first supernatant at step 401 by the centrifugation machine/device at 3,000-10,000×g for 30 minutes to obtain a second supernatant in the upper phase.

According to the preferred embodiment of the present invention, centrifuging the first supernatant by the centrifugation machine/device at 3,000-5,000×g.

At step 403, filtering the second supernatant at step 402 by a filter membrane with a pore size of 0.22 µm to obtain a filtered solution containing exosomes.

Finally, at step 404, treating the filtered solution containing exosomes at step 403 by enzyme Benzonase© at a concentration ranging from 0.2 U/mL to 1 U/mL for 2 hours to obtain the sample 400.

The experiment results demonstrate the effectiveness of removing free DNA in the cell culture medium when treating the filtered solution containing exosomes with enzyme Benzonase© compared to untreated samples, as indicated by the DNA contaminant ratio (%) presented in Table 2.

TABLE 2

Results of DNA contaminant ratio in the filtered exosome solution under various experimental conditions

| Experimental condition | Treatment | DNA contaminant ratio (%) |
| --- | --- | --- |
| Conditioned medium | The filtered solution containing exosomes | 100 |
| TFF | The filtered solution containing exosomes is filtered using the tangential flow filtration device | 36 |
| TFF + Benzonase | The filtered solution containing exosomes is treated with enzyme Benzonase ® at a concentration of 0.5 U/mL for 2 hours, and then filtered using the tangential flow filtration device | 2 |

Figure 6:
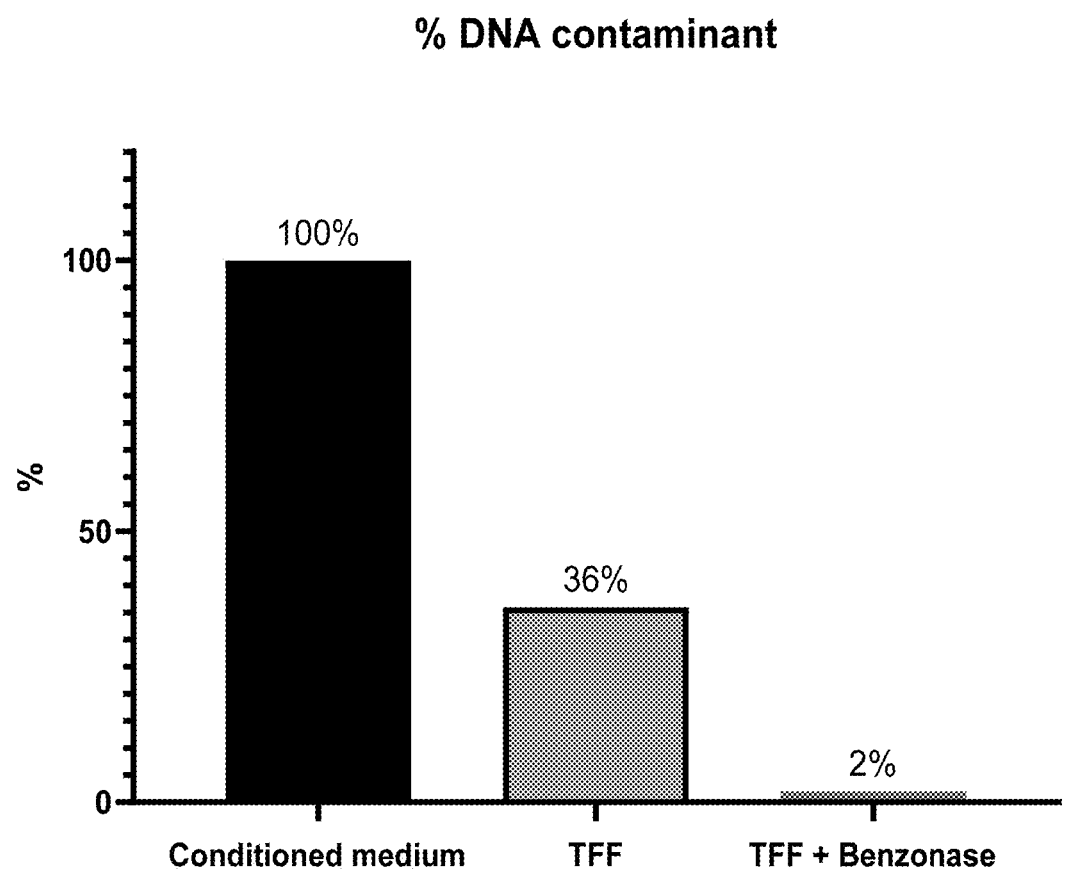
FIG. 6 is a chart illustrating the results of the experiment demonstrating the effectiveness of removing free DNA in the cell culture medium when treating the filtered solution containing exosomes with enzyme Benzonase© according to the first process compared to untreated samples.

Based on Table 2, the DNA contaminant ratio in the Conditioned medium condition was 100%. In the TFF condition, filtering the filtered solution containing exosomes using a tangential flow filtration machine/device reduced the DNA contaminant ratio to 36%. In the TFF+Benzonase condition, treating the filtered solution containing exosomes with enzyme Benzonase© at concentrations ranging from 0.5 U/mL for 2 hours, followed by filtration by the tangential flow filtration machine/device, achieved the most effective DNA removal. The resulting DNA contaminant ratio was only 2% (referenced by FIG. 6).

Figure 7:
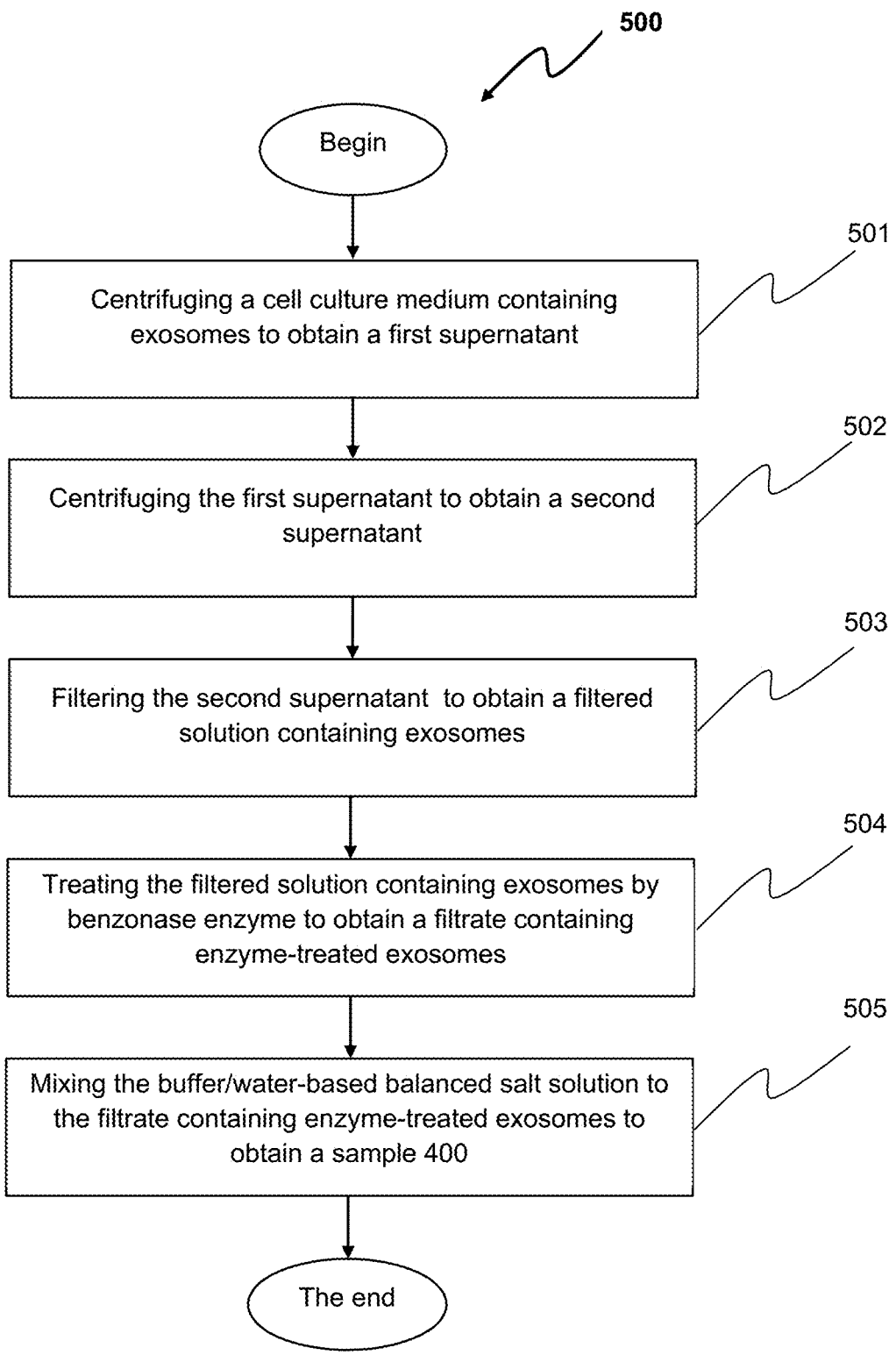
FIG. 7 is a flowchart illustrating a second process creating the sample 400 according to the embodiment of the invention.

According to another embodiment of the present invention, the sample 400, mentioned in methods 100, 200, and 300 is obtained from a second process 500 ("process 500") as referenced in FIG. 7. The process 500 consists of the following five steps: step 501, step 502, step 503, step 504, and step 505. At step 501, creating a first supernatant in the upper phase; wherein at step 501 having specification, and be done similarly at step 401 according the process 400 described above.

At step 502, creating a second supernatant in the upper phase by centrifuging the first supernatant at step 501; wherein step 502 having specification, and be done similarly at step 402 according the process 400 described above.

At step 503, creating a filtered solution containing exosomes by filtering the second supernatant at step 502; wherein step 503 having specification, and be done similarly at step 403 according the process 400 described above.

At step 504, treating the filtered solution containing exosomes at step 503 by enzyme Benzonase© at a concentration ranging from 0.2 U/mL to 1 U/mL for 2 hours to obtain a filtrate containing enzyme-treated exosomes.

Finally, at step 505, mixing the buffer/water-based balanced salt solution to the filtrate containing enzyme-treated exosomes at step 504 at a ratio of (1-3) parts of the buffer/water-based balanced salt solution to 1 part of filtrate containing enzyme-treated exosomes to create the sample 400.

According to the preferred embodiment of the present invention, at step 505, the buffer/water-based balanced salt solution is Phosphate Buffered Saline (PBS).

In the embodiment of the present invention, the sample obtained from process 500 is used for more efficient exosome purification compared to the sample 400 obtained from process 400 based on the evaluation criteria for comparison, including CD81 marker testing, TFF membrane congestion level, particle yield, and purity. The data for these evaluation criteria were collected in an experimental study to investigate the effectiveness of adding buffer/balanced salt solution to the enzyme-treated exosome-containing filtrate (Dilution condition) compared to not adding any solution (No dilution condition) during the tangential flow filtration stage. The results of the experiment are presented in Table 3.

TABLE 3

Results of TFF membrane congestion level, CD81 marker testing, exosome particle yield, and purity of the obtained exosomes in two experimental conditions

| Experimental condition | CD81 marker testing | TFF membrane congestion level (%) | Particle yield (%) | Purity (fold change) |
|---|---|---|---|---|
| Dilution | + | 36 | 100 | 1.0 |
| No dilution | + | 86 | 93 | 0.95 | in which:
(+) means that the CD81 marker testing yields a positive result; dilution is the sample 400 obtained from process 500; and no dilution is the sample 400 obtained from process 400.

Figure 8:
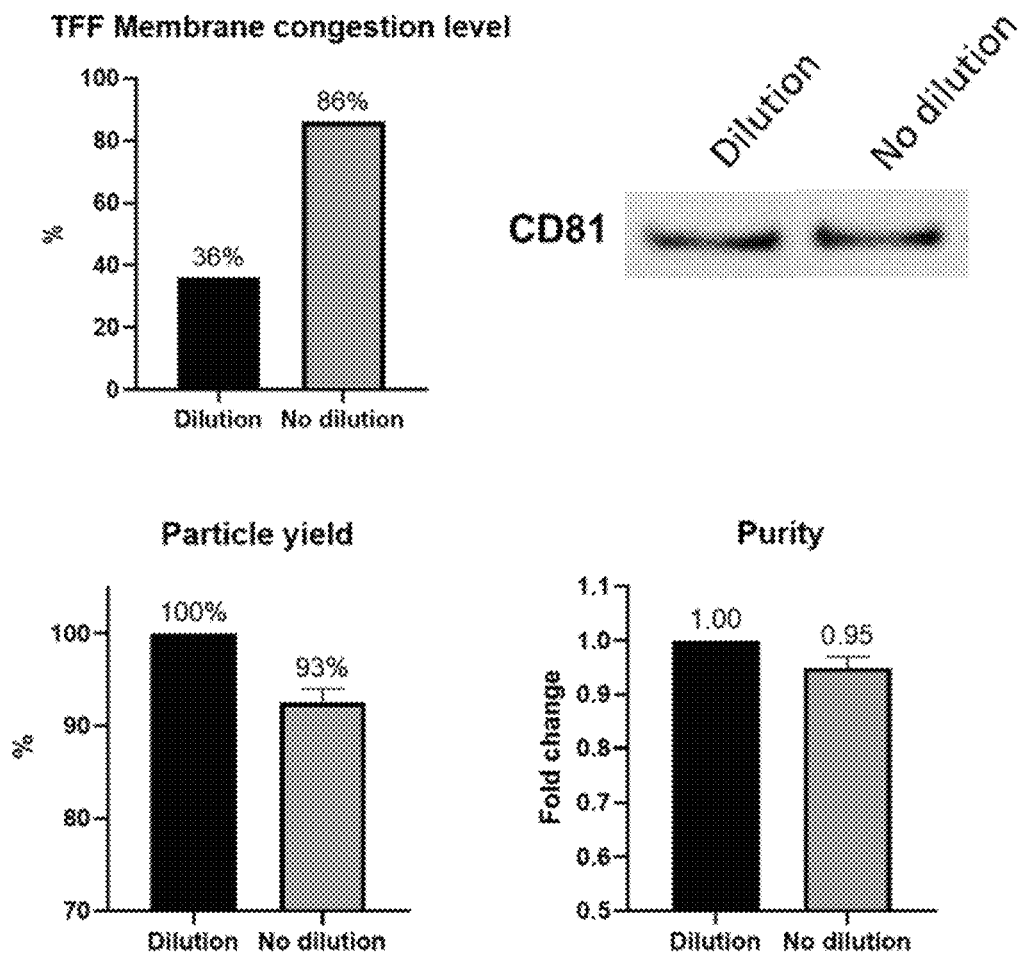
FIG. 8 is a chart illustrating the results of the experimental study investigating the effectiveness of the sample 400 obtained from the first process compared to the sample 400 obtained from the second process according to the embodiment of the invention.

Based on Table 3, the results of CD81 marker testing show positive results in both conditions, indicating the presence of exosomes in both cases. The evaluation of the TFF membrane congestion level reveals that in the Dilution condition (with adding a buffer/water-based balanced salt solution), the TFF membrane congestion level is 36%. In contrast, in the No dilution condition (without adding the buffer/water-based balanced salt solution), the TFF membrane congestion level is higher at 86%. The assessment of exosome particle yield demonstrates a 100% yield in the Dilution condition, while the No dilution condition exhibits a lower yield of 93%. The evaluation of exosome purity indicates a 1.0-fold change in the Dilution condition, whereas the No dilution condition shows a 0.95-fold change (referenced by FIG. 8).

Figure 9:
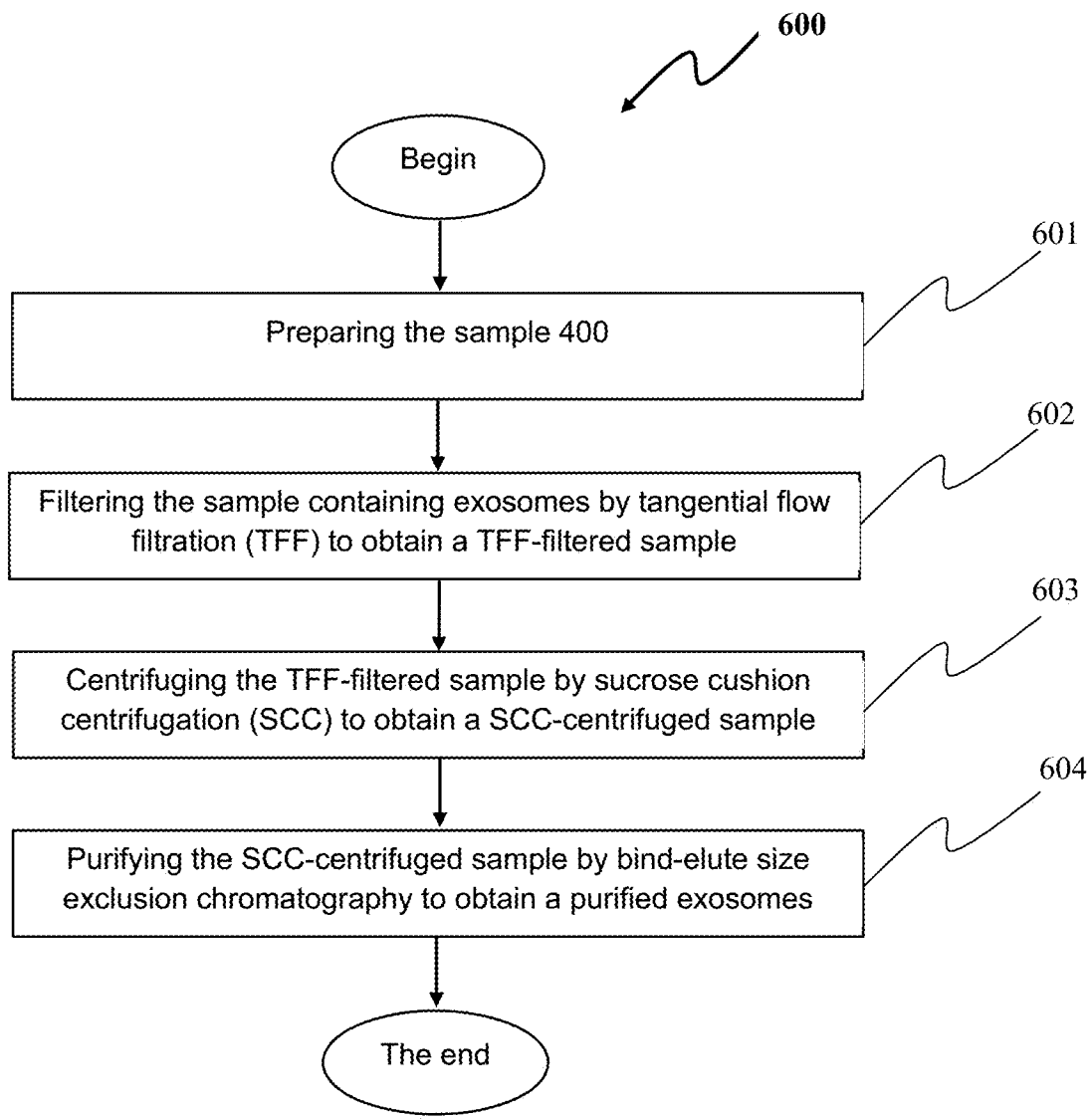
FIG. 9 is a flowchart illustrating a process for purifying exosomes from a cell culture medium according to the method 100 in accordance with an exemplary embodiment of the present invention.

Referring to FIG. 9, a process for purifying exosomes from a cell culture medium 600 ("process 600") according to the method 100 in the preferred embodiment of the present invention. The process 600 starts with step 601, which involves preparing the sample 400.

According to the embodiment of the invention, the sample 400 is obtained from the process 400 described above.

According to another embodiment of the invention, the sample 400 is obtained from the process 500 described above.

According to the preferred embodiment of the present invention, the sample 400 obtained from process 500 better than the sample 400 obtained from process 400, wherein a comparison factor is based on CD81 marker testing, TFF membrane congestion level, particle yield, and purity.

At step 602, creating a TFF-filtered sample by filtering the sample 400 at step 601 by tangential flow filtration (TFF), comprising:
creating a first filtered sample containing exosomes by filtering the sample 400 until the volume of the sample 400 is reduced from 10 to 20 times; and creating the TFF-filtered sample by diafiltrating the first filtered sample containing exosomes two (02) times, comprising:
a first time: mixing the buffer/water-based balanced salt solution to the first filtered sample containing exosomes at a ratio of 1:1 to obtain a first temporary mixture, then filtering the first temporary mixture until the volume of the first temporary mixture is reduced by 50 percent to obtain a second filtered sample containing exosomes; and
a second time: mixing the buffer/water-based balanced salt solution to the second filtered sample containing exosomes at a ratio of 1:1 to obtain a third temporary mixture, then filtering the third temporary mixture until the volume of the third temporary mixture is reduced by 50 percent to obtain the TFF-filtered sample.

According to the embodiment of the invention, the machine/device used in step 602 is the tangential flow filtration machine/device with the following set parameters: a pore size of 300 kDa, a feed flow rate of 25 mL/minute, and a transmembrane pressure of 0.7 bar-1.0 bar.

At step 603, centrifuging the TFF-filtered sample at step 602 by sucrose cushion centrifugation (SCC) to obtain a SCC-centrifuged sample, comprising:
centrifuging the centrifuge tube containing 8 parts of the TFF-filtered sample at stage (A) and 2 parts of 30% sucrose solution at 100,000-130,000×g for at least 3 hours at 4° C.; then removing 6-7 parts of the solution from the upper phase of the centrifuge tube, collecting the sucrose fraction containing exosomes in the remaining 3-4 parts at the bottom of the centrifuge tube;
mixing 6-7 parts the Phosphate Buffered Saline (PBS) buffer with the sucrose fraction containing exosomes to obtain the foundation solution; and
centrifuging the foundation solution at 100,000-130,000×g for 3 hours at 4° C., removing the liquid phase to obtain the SCC-centrifuged sample;

In the embodiment of the present invention, centrifuging the TFF-filtered sample in a 30% sucrose solution provides better purification efficiency of exosomes compared to a 40% sucrose solution, as evaluated by CD81 marker testing, particle yield, and purity. The data for these evaluation criteria were obtained from an experimental study investigating the effect of sucrose concentration during the sucrose cushion centrifugation stage, and are presented in Table 4.

TABLE 4

Experimental results comparing the effects of 30% sucrose (UC30 condition) and 40% sucrose (UC40 condition) during the sucrose cushion centrifugation stage on exosome purification efficiency

| Experimental condition | CD81 marker testing | Particle yield (%) | Purity (fold change) |
|---|---|---|---|
| UC30 | + | 100 | 1.0 |
| UC40 | + | 69 | 0.4 | in which:
(+) means that the CD81 marker testing yields a positive result.

Figure 10:
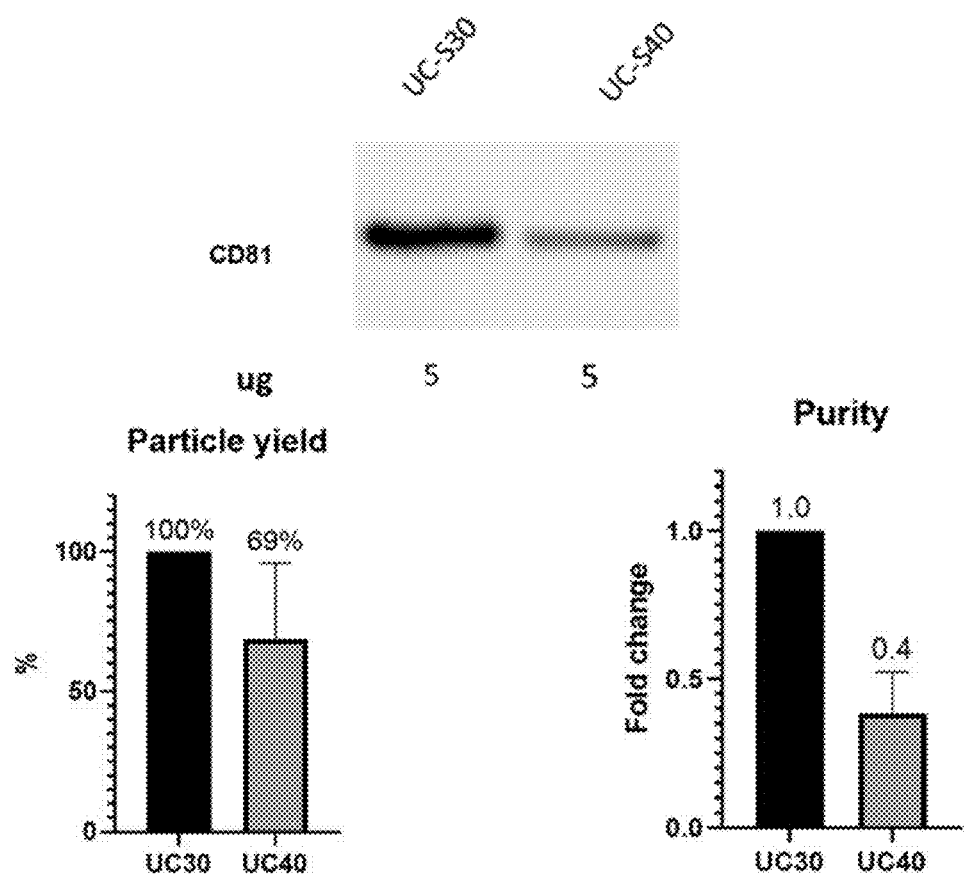
FIG. 10 is a chart illustrating the results of an experimental study investigating the effect of sucrose concentration during the sucrose cushion centrifugation stage.

Based on Table 4, the results of CD81 marker testing were positive in both conditions, indicating the presence of exosomes in both UC30 and UC40 conditions. The evaluation of particle yield showed that the UC30 condition achieved a 100% particle yield, while the UC40 condition had a lower particle yield of 69%. The assessment of exosome purity revealed a fold change of 1.0 in the UC30 condition, indicating high purity. In contrast, the UC40 condition had a lower fold change of 0.4, indicating lower purity (referenced by FIG. 10).

According to the preferred embodiment of the present invention, centrifuging the TFF-filtered sample by sucrose cushion centrifugation (SCC) by the centrifugation machine/device using a fixed-angle rotor yields better exosome purification efficiency than a swing-out rotor. This conclusion is based on the evaluation of particle yield and purity. The data for these evaluation criteria were obtained from an experiment comparing the rotor types used in the centrifuge during the sucrose cushion centrifugation stage and are presented in Table 5.

TABLE 5

Results of particle yield and purity of the obtained exosomes when using a Fixed-angle rotor (Fixed condition) and a Swing-out rotor (Swing condition)

| Experimental condition | Particle yield (%) | Purity (fold change) |
|---|---|---|
| Fixed | 100 | 1.0 |
| Swing | 47 | 0.95 |

Figure 11:
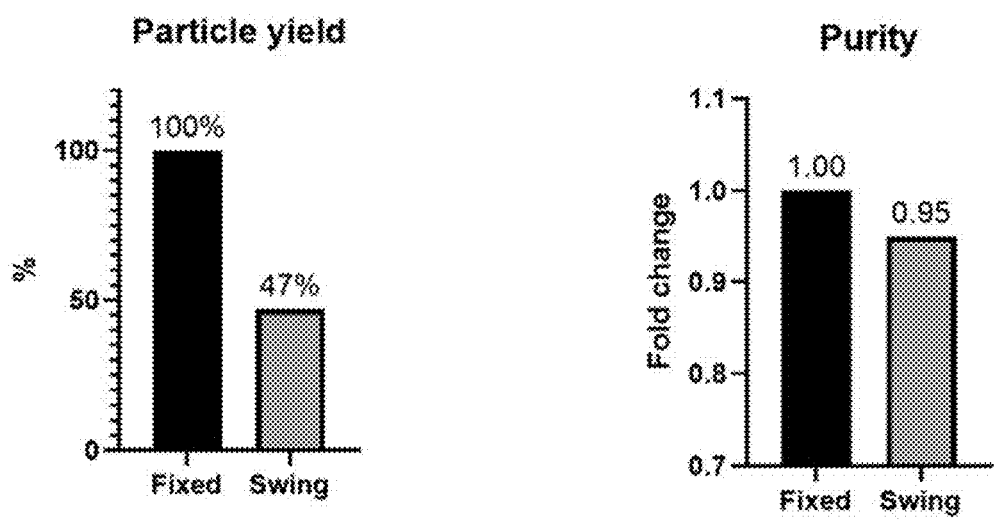
FIG. 11 is a chart illustrating the results of an experiment comparing the rotor types used in the centrifuge during the sucrose cushion centrifugation stage.

Based on Table 5, the evaluation results for exosome recovery efficiency show that the Fixed condition achieves a particle yield of 100%. In contrast, the Swing condition has a lower particle yield of 47%. The evaluation results for exosome purity indicate that the Fixed condition has a purity level of 1.0 fold change. In comparison, the Swing condition has a purity level of 0.95 fold change (referenced by FIG. 11).

Finally, at step 604, purifying the SCC-centrifuged sample at step 603 by bind-elute size exclusion chromatography (BE-SEC) by the size exclusion chromatography machine/device in a specific order comprising:

mixing the Phosphate Buffered Saline (PBS) buffer into the SCC-centrifuged sample at stage (B) to obtain a suspension containing exosomes; and loading the suspension containing exosomes into a chromatography column containing 1-20 mL of resin beads at a rate of 0.5-1.5 mL/minute, and purifying to obtain a purified exosomes, comprising the following three steps:

step 1: recovering a first fraction based on the UV 280 nm peak signal at a recovery rate of 0.5-1.5 mL/minute;

step 2: further recovering a second fraction containing 10 mL after the UV 280 nm peak signal at a recovery rate of 0.5-1.5 mL/minute; and step 3: creating the purified exosomes by mixing the first fraction based on the UV 280 nm peak signal and the second fraction containing 10 mL after the UV 280 nm peak signal.

The embodiment of the present invention involves the additional recovery of a second fraction containing 10 mL after the UV 280 nm signal, which improves the efficiency of exosome purification based on evaluation criteria, including CD81 marker testing and particle yield. The evaluation data for these criteria were obtained through experiments assessing the effectiveness of the additional recovery of a second fraction containing 10 mL after the UV 280 nm signal and are presented in Table 6.

TABLE 6

Results of the evaluation of the efficiency of additional recovery of a second fraction containing 10 mL after the UV 280 nm signal

| Experimental condition | CD81 marker testing | Particle yield (%) |
|---|---|---|
| Exosome peak fraction | + | 98 |
| Extra 10 mL fraction | + | 2 | in which:
(+) means that the CD81 marker testing yields a positive result; Exosome peak fraction: is the first fraction; and Extra 10 mL fraction: is the second fraction.

Figure 12:
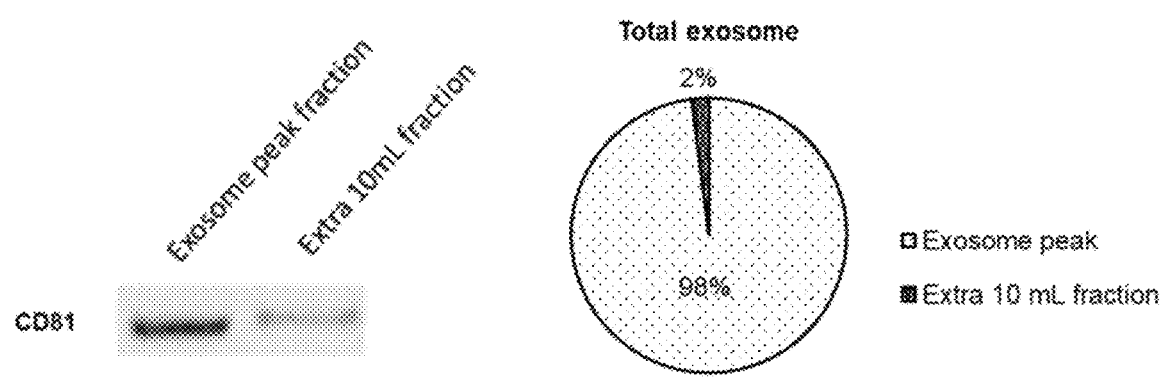
FIG. 12 is a chart illustrating the results of the experiments assessing the effectiveness of the additional recovery of a second fraction containing 10 mL after the UV 280 nm signal.

Based on Table 6, the results of CD81 marker testing are positive in both the exosome peak fraction (recovery of the first fraction based on the UV 280 nm signal) and the extra 10 mL fraction (recovery of an additional second fraction containing 10 mL after the UV 280 nm signal), indicating the presence of exosomes in both fractions. Regarding particle yield, the exosome peak fraction accounts for 98%, while the extra 10 mL fraction accounts for 2% of the total exosome content (referenced by FIG. 12).

According to the preferred embodiment of the present invention, the size-exclusion chromatography machine/device using a column containing 5 mL resin beads achieves better exosome purity than a column containing 10 mL resin beads, based on the evaluated criteria of particle yield and purity. The data for these evaluation criteria were obtained from experiments investigating the impact of column volume on the efficiency of exosome purification by the size-exclusion chromatography device and are presented in Table 7.

TABLE 7

Results of particle yield and purity of exosomes using a column containing 5 mL resin beads and 10 mL resin beads

| Experimental condition | Particle yield (%) | Purity (fold change) |
|---|---|---|
| 5 mL resin | 100 | 1.0 |
| 10 mL resin | 46 | 0.8 |

Figure 13:
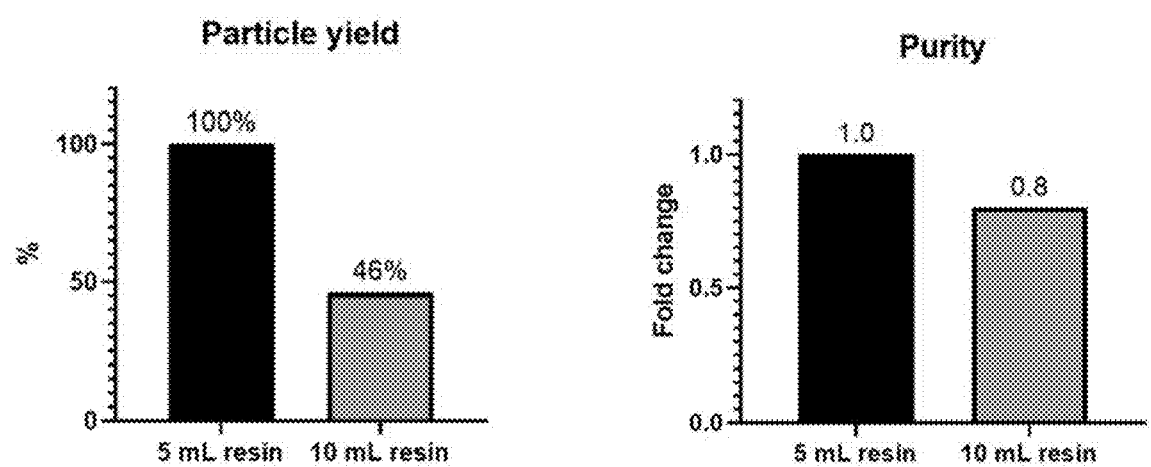
FIG. 13 is a chart illustrating the results of experiments investigating the impact of column volume on the efficiency of exosome purification using the size-exclusion chromatography device.

Based on Table 7, the results of particle yield show that the 5 mL resin condition achieves a yield of 100% for exosomes. In contrast, the 10 mL resin condition yields a lower particle yield of 47%. The evaluation of exosome purity reveals a fold change of 1.0 for the 5 mL resin condition, while the 10 mL resin condition yields a fold change of 0.8 (referenced by FIG. 13).

Figure 14:
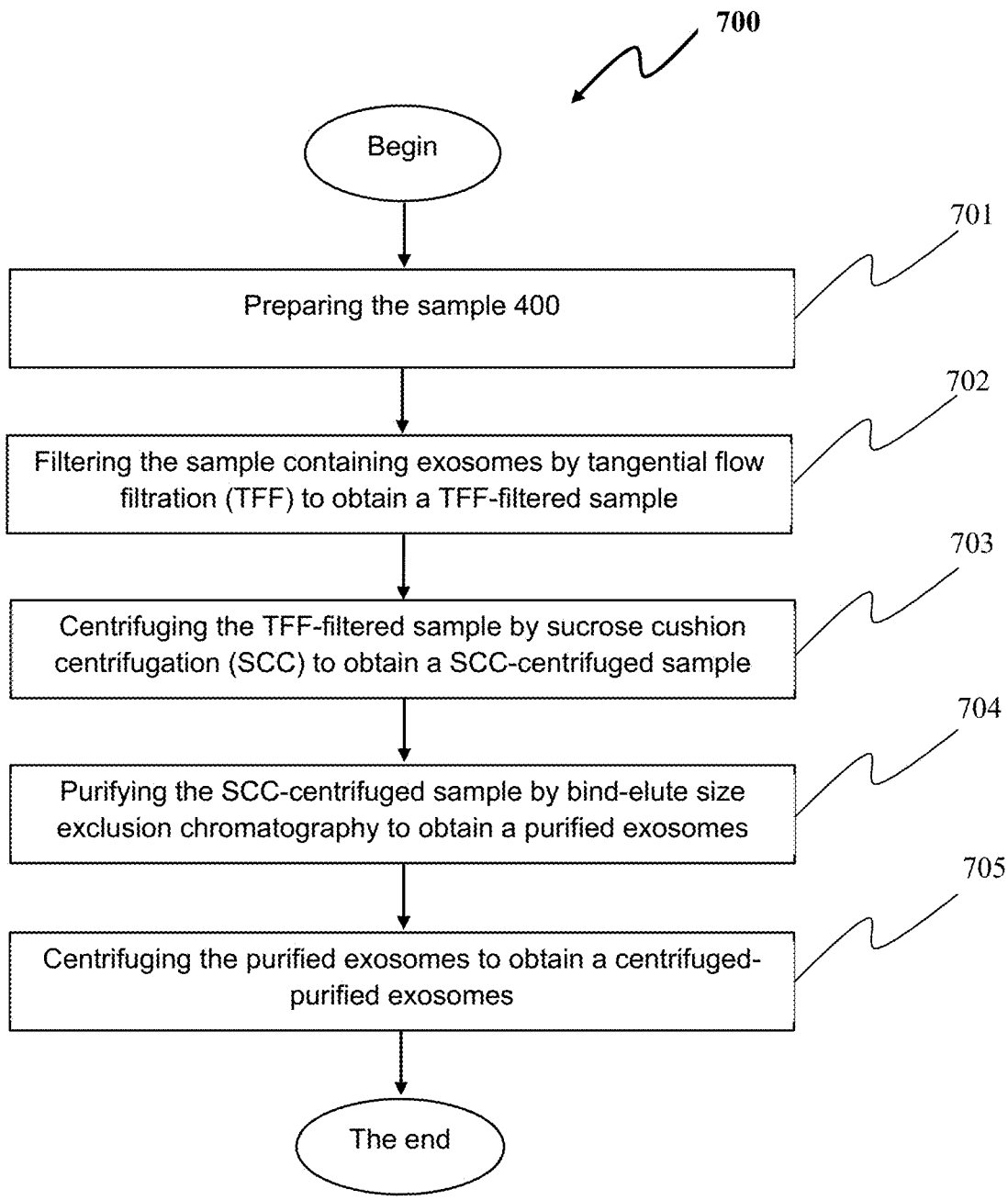
FIG. 14 is a flowchart illustrating a process for purifying exosomes from a cell culture medium according to the method 200 in accordance with an exemplary embodiment of the present invention.

Referring to FIG. 14 a process for purifying exosomes from a cell culture medium 700 ("process 700") according to the method 200 in the preferred embodiment of the present invention. The process 700 is a variant of the process 600 with the additional inclusion of centrifuging the purified exosomes to obtain a centrifuged-purified exosomes. According to the embodiment of the invention, the process 700 consists of five steps in a specific order including: a step 701, a step 702, a step 703, a step 704, and a step 705; wherein at step 701, preparing the sample 400; wherein step 701 having specification, and be done similarly at step 601 according the process 600 described above;

at step 702, creating a TFF-filtered sample by filtering the sample 400 at step 701; wherein step 702 having specification, and be done similarly at step 602 according the process 600 described above;

at step 703, creating a SCC-centrifuged sample by centrifuging the TFF-filtered sample at step 702; wherein step 703 having specification, and be done similarly at step 603 according the process 600 described above;

at step 704, creating a purified exosomes by purifying the SCC-centrifuged sample at step 703; wherein step 704 having specification, and be done similarly at step 604 according the process 600 described above; and at step 705, centrifuging the purified exosomes at step 704 by the centrifugation machine/device using a fixed-angle rotor at 100,000-130,000×g for 3 hours at 4° C., removing the supernatant to obtain the centrifuged-purified exosomes.

Figure 15:
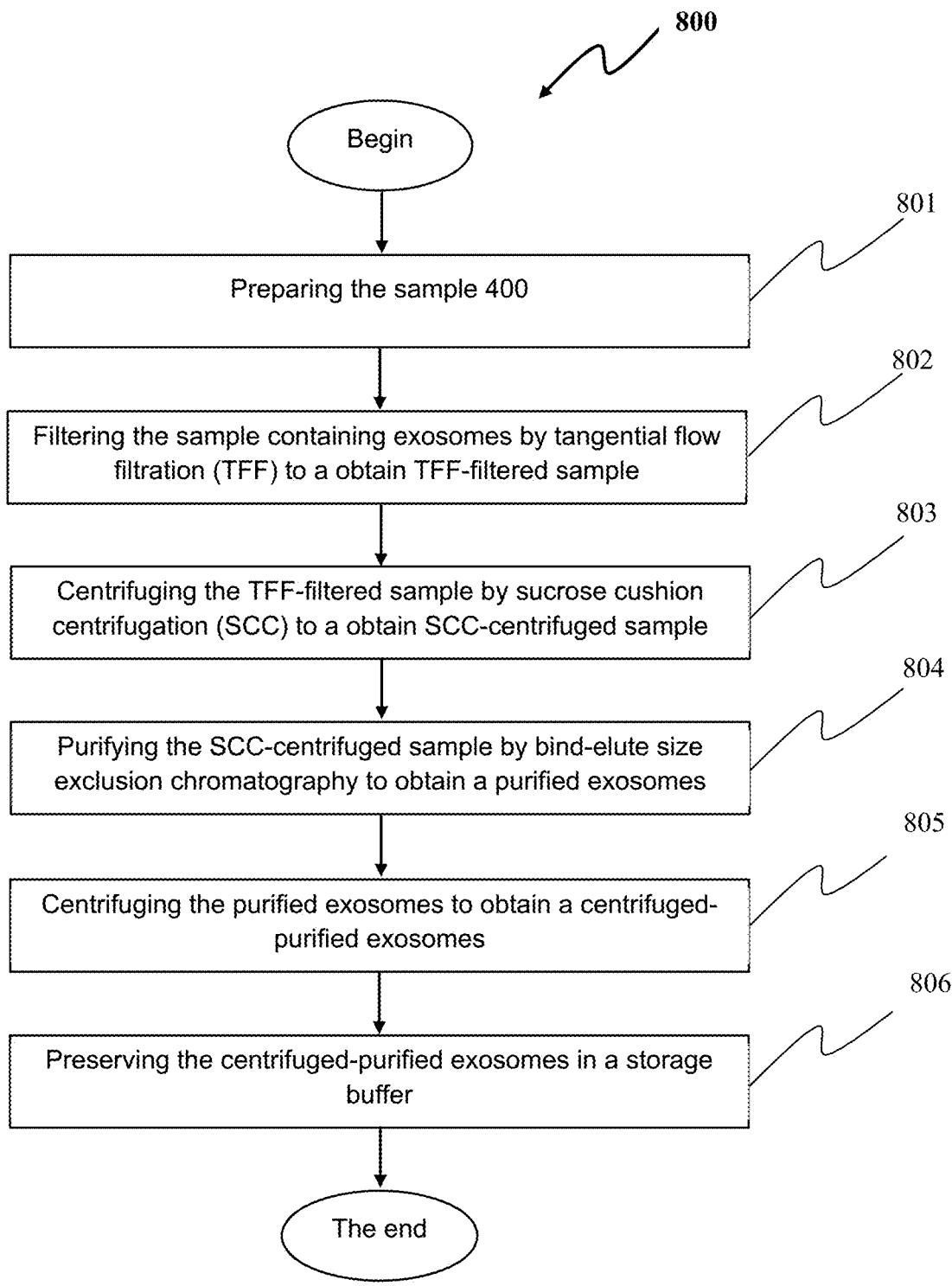
FIG. 15 is a flowchart illustrating a process for purifying exosomes from a cell culture medium according to the method 300 in accordance with an exemplary embodiment of the present invention.

Referring to FIG. 15, a process for purifying exosomes from a cell culture medium 800 ("process 800") according to the method 300 in the preferred embodiment of the present invention. The process 800 is a variant of the process 700 with the additional inclusion of preserving the centrifuged exosomes in a storage buffer. According to the embodiment of the invention, the process 800 consists of five steps in a specific order including: a step 801, a step 802, a step 803, a step 804, a step 805, and a step 806; wherein at step 801, preparing the sample 400; wherein step 801 having specification, and be done similarly at step 601 according the process 600 described above;

at step 802, creating a TFF-filtered sample by filtering the sample 400 at step 801; wherein step 802 having specification, and be done similarly at step 602 according the process 600 described above;

at step 803, creating a SCC-centrifuged sample by centrifuging the TFF-filtered sample at step 802; wherein step 803 having specification, and be done similarly at step 603 according the process 600 described above;

at step 804, creating a purified exosomes by purifying the SCC-centrifuged sample at step 803; wherein step 804 having specification, and be done similarly at step 604 according the process 600 described above;

at step 805, creating a centrifuged-purified exosomes by centrifuging the purified exosomes at step 804; wherein step 805 having specification, and be done similarly at step 705 according the process 700 described above; and at step 806, preserving the centrifuged-purified exosomes at step 805 in the storage buffer; wherein the storage buffer contains human serum albumin component with a concentration ranging from 0.05% to 0.3% by weight of the storage buffer.

According to the preferred embodiment of the present invention, the storage buffer also containing chemical components consisting of an elemental sodium (Na) having 150-250 mmol/l, an elemental potassium (K) having 4 mmol/l, an elemental magnesium (Mg) having 1 mmol/l, an elemental calcium (Ca) having 2.5 mmol/l, an elemental chloride (Cl) having 130-230 mmol/l, an elemental acetate ($C_2H_3O$) having 24 mmol/l, and an elemental maleate ($C_4H_2O_4$) having 5 mmol/l.

Preserving exosomes in a storage buffer containing human serum albumin improves stability compared to a storage buffer without human serum albumin, as assessed by CD81 marker testing and intensity measurements. The data for these evaluation parameters were obtained from an experiment comparing the effectiveness of preserving exosomes in different storage buffer formulations, as presented in Table 8.

TABLE 8

Results of CD81 marker testing and intensity when preserving exosomes in different storage buffer formulations

| Experimental condition | Treatment | CD81 marker testing | Intensity (%) |
|---|---|---|---|
| PBS fresh | Exosomes were dissolved in PBS buffer | + | 100 |
| PBS fresh 4-1w | Exosomes were dissolved in PBS buffer and stored at 4° C. for 1 week | + | 72 |
| Storage buffer 1 fresh | Exosomes were dissolved in Storage buffer 1 | + | 100 |
| Storage buffer 1-4-1w | Exosomes were dissolved in Storage buffer 1 and stored at 4° C. for 1 week | + | 95 |
| Storage buffer 2 fresh | Exosomes were dissolved in Storage buffer 2 | + | 100 |
| Storage buffer 2-4-1w | Exosomes were dissolved in Storage buffer 2 | + | 105 | in which:
(+) means that the CD81 marker testing yields a positive result;

Storage buffer 1 has the composition as shown in Table 9, and Storage buffer 2 has the composition as shown in Table 10.

TABLE 9

Composition of Storage buffer 1

| Active substance | Electrolyte concentrations | | |
|---|---|---|---|
| Sodium chloride | 7.0 g/L | Sodium ($Na^+$) | 150.0 mmol/l |
| Potassium chloride | 0.30 g/L | Potassium ($K^+$) | 4.0 mmol/l |
| Magnesium chloride hexahydrate | 0.20 g/L | Magnesium ($Mg^{2+}$) | 1.0 mmol/l |
| Calcium chloride dehydrate | 0.37 g/L | Calcium ($Ca^{2+}$) | 2.5 mmol/l |
| | | Chloride ($Cl^-$) | 130.0 mmol/l |
| Sodium acetate trihydrate | 3.27 g/L | Acetate ($C_2H_3O^{2-}$) | 24.0 mmol/l |
| L-Malic acid | 0.67 g/L | Malate ($C_4H_2O_4^{2-}$) | 5.0 mmol/l |

TABLE 10

Composition of Storage buffer 2

| Active substance | Electrolyte concentrations | | |
|---|---|---|---|
| Sodium chloride | 7.0 g/L | Sodium ($Na^+$) | 150.0 mmol/l |
| Potassium chloride | 0.30 g/L | Potassium ($K^+$) | 4.0 mmol/l |
| Magnesium chloride hexahydrate | 0.20 g/L | Magnesium ($Mg^{2+}$) | 1.0 mmol/l |
| Calcium chloride dehydrate | 0.37 g/L | Calcium ($Ca^{2+}$) | 2.5 mmol/l |
| | | Chloride ($Cl^-$) | 130.0 mmol/l |
| Sodium acetate trihydrate | 3.27 g/L | Acetate ($C_2H_3O^{2-}$) | 24.0 mmol/l |
| L-Malic acid | 0.67 g/L | Malate ($C_4H_2O_4^{2-}$) | 5.0 mmol/l |
| Human serum albumin | 2.0 g/L | | |

Figure 16:
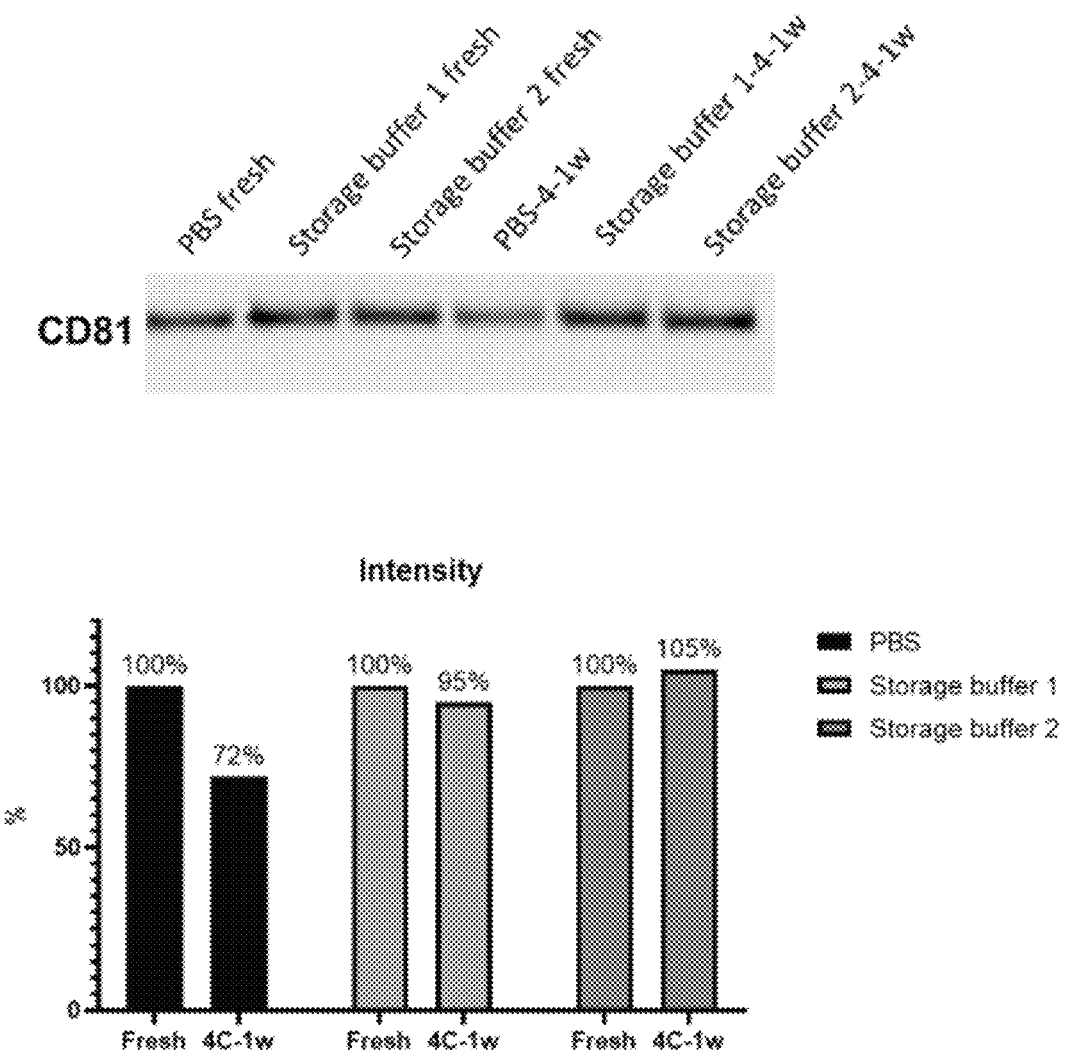
FIG. 16 is a chart illustrating the results of an experiment comparing the effectiveness of preserving exosomes in different storage buffer formulations.

Based on Table 8, the results of CD81 marker testing show positive results for all experimental formulations. Regarding intensity evaluation, when preserving exosomes in PBS buffer (PBS fresh and PBS fresh 4-1w formulations), the intensity decreased by 28% after 1 week of storage at 4° C. On the other hand, when preserving exosomes in Storage buffer 1 (Storage buffer 1 fresh and Storage buffer 1-4-1w formulations), the intensity decreased by 5% after 1 week of storage at 4° C. When preserving exosomes in Storage buffer 2 (Storage buffer 2 fresh and Storage buffer 2-4-1w formulations), the intensity increased, reaching 105% after 1 week of storage at 4° C. (referenced by FIG. 16).

Figure 17:
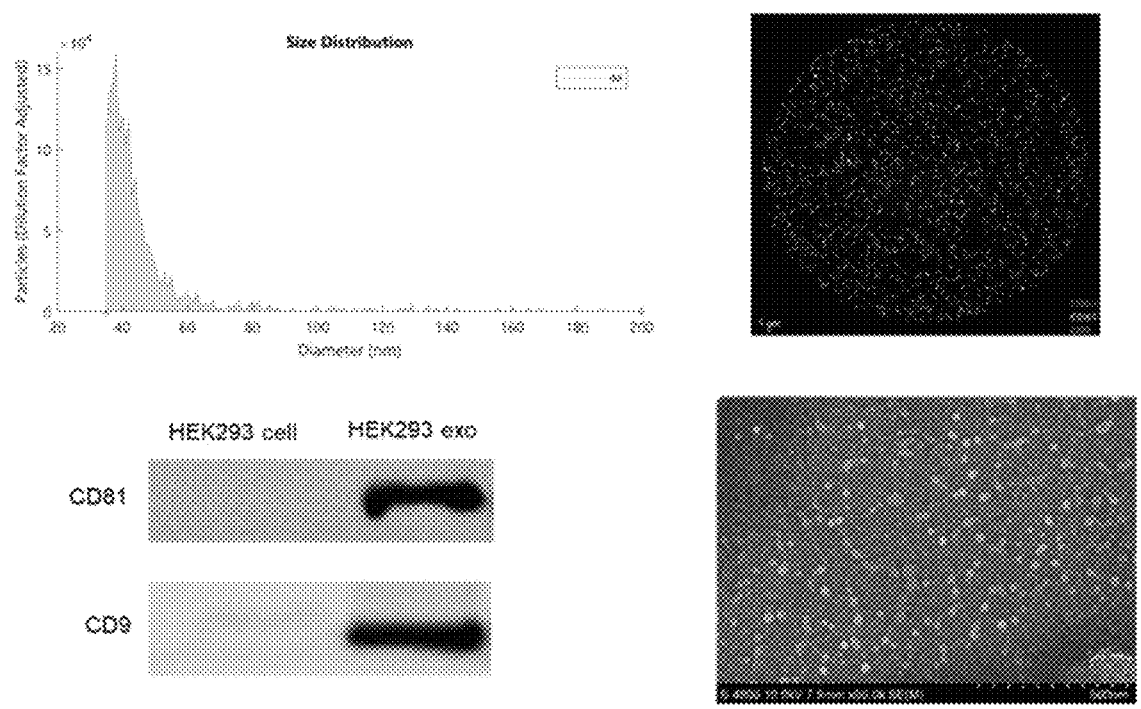
FIG. 17 is a graph and image depicting the analysis results of the characteristics of exosomes.

The exosomes obtained from the process 800 were analyzed for various characteristics, including size, integrity of shape, testing of characteristic exosomal markers including CD81, CD9, and CD63, and purity. The analysis results regarding size and integrity of shape showed that the exosomes had a size distribution ranging from 35-100 nm, with a median size of 46 nm. Furthermore, the exosomes remained intact, as demonstrated by the scanning electron micrograph. The testing of characteristic exosomal markers, including CD81, CD9, and CD63, all showed positive results. The purity of the exosomes reached at least $1\times10^{10}$ particles/µg protein (referenced by FIG. 17).

The exosomes obtained from process 600 did not affect the viability of primary human T-lymphocytes, as assessed by the cell death/survival ratio of CD3+ T-cells. The data regarding the cell death/survival ratio of CD3+ T-cells were obtained from an experiment evaluating the influence of exosomes at different concentrations on the survival capability of T-lymphocytes and is presented in Table 11.

TABLE 11

Results of the cell viability ratio of CD3+ T-cell in various experimental conditions

| Experimental condition | Treatment | Cell viability after 48 h (%) |
|---|---|---|
| Control | CD3+ T-cell culture plates without exosome supplementation | 100 |
| 1.E+06 particles | CD3+ T-cell culture plates supplemented with exosomes at a concentration of $10^6$ particles | 102 |
| 1.E+07 particles | CD3+ T-cell culture plates supplemented with exosomes at a concentration of $10^7$ particles | 104 |
| 1.E+08 particles | CD3+ T-cell culture plates supplemented with exosomes at a concentration of $10^8$ particles | 98 |
| 1.E+09 particles | CD3+ T-cell culture plates supplemented with exosomes at a concentration of $10^9$ particles | 99 | in which:
the density of CD3+ T cells in the experimental conditions was $1.0 \times 10^6$ cells/mL.

Figure 18:
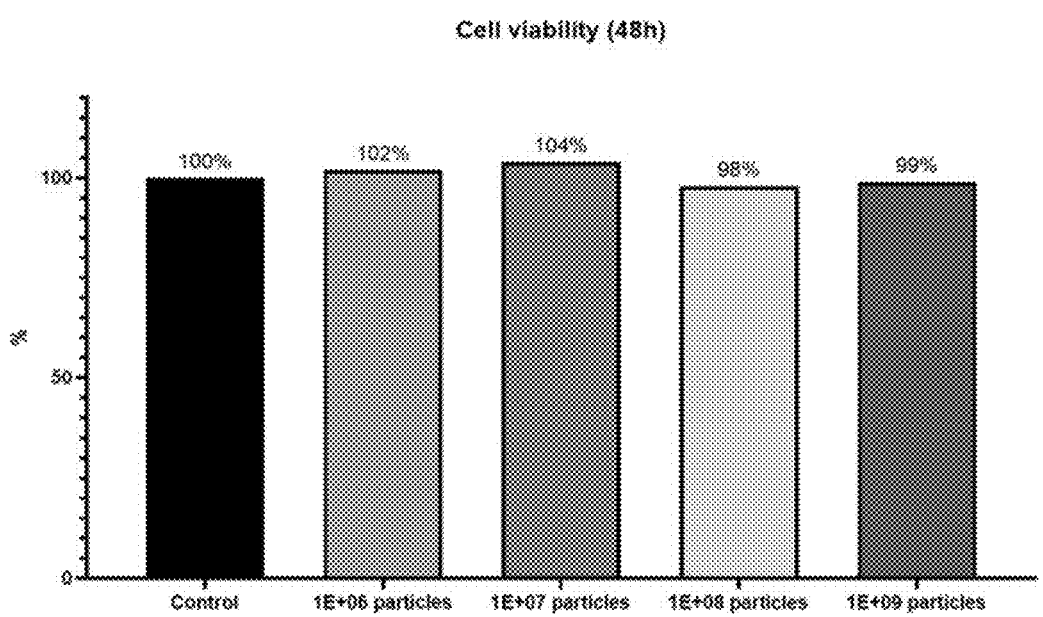
FIG. 18 is a chart illustrating the results of an experiment evaluating the influence of exosomes at different concentrations on the survival capability of T-lymphocytes.

Based on the data presented in Table 11, the viability of CD3+ T-cell cultures were evaluated after 48 hours of incubation at 37° C. with 5% $CO_2$. The cell viability was determined by counting the ratio of live to dead cells in the test plates using Trypan Blue staining. The results demonstrated that the cell viability ratios in Control, 1.E+06 particles, 1.E+07 particles, 1.E+08 particles, and 1.E+09 particles conditions were 100%, 102%, 104%, 98%, and 99%, respectively (referenced by FIG. 18).

Exosomes obtained from the process 800 did not activate primary human macrophages, as indicated by the mRNA expression levels of IL-6 and TNF-alpha in macrophages. The data of this evaluation were obtained from an experiment assessing the influence of exosomes on macrophage activity and is presented in Table 12.

TABLE 12

Results of mRNA expression levels of IL-6 and TNF-alpha in different experimental conditions

| Experimental condition | Treatment | Macrophage activation | |
|---|---|---|---|
| | | TNF-alpha (%) | IL-6 (%) |
| Control | Macrophage cell culture plates were not supplemented with exosomes | 0 | 0 |
| 1.E+06 particles | Macrophage cell culture plates were supplemented with exosomes at a concentration of $10^6$ particles | 0 | 0 |
| 5.E+07 particles | Macrophage cell culture plates were supplemented with exosomes at a concentration of $5 \times 10^7$ particles | 4 | 2 |
| LPS 1 ng/mL | Lipopolysaccharide (LPS) was added at a concentration of 1 ng/mL | 53 | 66 |
| LPS 10 ng/mL | Lipopolysaccharide (LPS) was added at a concentration of 10 ng/mL | 100 | 100 | in which:
the cell density of Macrophages in the experimental conditions was $3 \times 10^5$ cells/mL, and Lipopolysaccharide (LPS) was used as a positive control.

Figure 19:
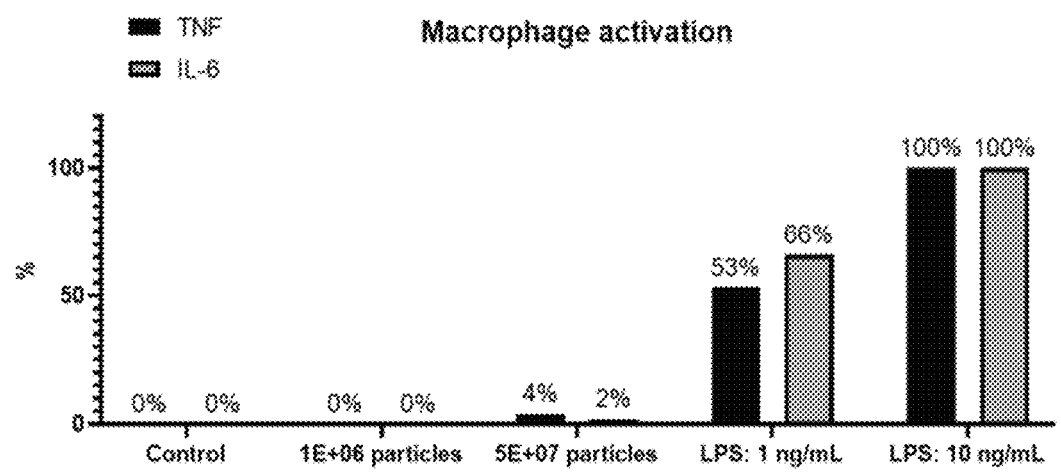
FIG. 19 is a chart illustrating the results of an experiment assessing the influence of exosomes on macrophage activity.

Based on Table 12, after 48 hours of incubating the cultured macrophage cells under different experimental conditions at 37° C. with 5% $CO_2$, RNA was extracted and RT-qPCR was performed to assess the mRNA expression levels of IL-6 and TNF-alpha. The results showed that the TNF-alpha expression levels in control, 1.E+06 particles, 5.E+07 particles, LPS 1 ng/mL, and LPS 10 ng/mL conditions were 0%, 0%, 4%, 53%, and 100%, respectively. The IL-6 expression levels in the Control, 1.E+06 particles, 5.E+07 particles, LPS 1 ng/mL, and LPS 10 ng/mL conditions were 0%, 0%, 2%, 66%, and 100%, respectively (referenced by FIG. 19).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "includes" and/or "including," when used in this specification, specify the presence of stated features, integers, steps, operations, elements, and/or components, but do not preclude the presence or addition of one or more other features, integers, steps, operations, element components, and/or groups thereof.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The description of the present invention has been presented for purposes of illustration and description but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order, or steps may be added, deleted, or modified. All of these variations are considered a part of the claimed invention.

While the preferred embodiment to the invention had been described, it will be understood that those skilled in the art, both now and in the future, may make various improvements and enhancements which fall within the scope of the claims which follow. These claims should be construed to maintain the proper protection for the invention first described.

The foregoing description details certain embodiments of the invention. It will be appreciated, however, that no matter how detailed the foregoing appears in text, the invention can be practiced in many ways. As is also stated above, it should be noted that the use of particular terminology when describing certain features or aspects of the invention should not be taken to imply that the terminology is being re-defined herein to be restricted to including any specific characteristics of the features or aspects of the invention with which that terminology is associated. The scope of the invention should therefore be construed in accordance with the appended claims and any equivalents thereof.

What is claimed is:

1. A method for purifying exosomes from a cell culture medium comprising treating stages of a sample containing exosomes in the following specific order:
   (A) filtering the sample containing exosomes by tangential flow filtration (TFF) to obtain a TFF-filtered sample;
   (B) centrifuging the TFF-filtered sample by sucrose cushion centrifugation (SCC) to obtain a SCC-centrifuged sample;
   (C) purifying the SCC-centrifuged sample by bind-elute size exclusion chromatography (BE-SEC) to obtain a purified exosomes;
   (D) centrifuging the purified exosomes with the following set parameters: having a fixed-angle rotor at 100,000-130,000×g for 3 hours at 4° C., then removing the supernatant to obtain a centrifuged-purified exosomes; and
   (E) preserving the centrifuged-purified exosomes in a storage buffer;
   wherein the storage buffer comprising 7 g/L sodium chloride, 0.3 g/L potassium chloride, 0.2 g/L magnesium chloride hexahydrate having, 0.37 g/L calcium chloride dehydrate, 3.27 g/L sodium acetate trihydrate, 0.67 g/L L-Malic acid, and 2.0 g/L human serum albumin, all are mixed that the storage buffer containing electrolyte components consisting of an elemental sodium ($Na^+$) having 150-250 mmol/l, an elemental potassium ($K^+$) having 4 mmol/l, an elemental magnesium ($Mg^{2+}$) having 1 mmol/l, an elemental calcium ($Ca^{2+}$) having 2.5 mmol/l, an elemental chloride ($Cl^-$) having 130-230 mmol/l, an elemental acetate ($C_2H_3O^{2-}$) having 24 mmol/l, and an elemental malate ($C_4H_2O_4^{2-}$) having 5 mmol/l;
   in which, prepare the sample containing exosomes by performing in a specific order from (a') to (d') comprising:
   (a') centrifuging a cell culture medium containing exosomes at 300×g for 5 minutes to obtain a first supernatant in the upper phase;
   wherein the cell culture medium containing exosomes obtained by culturing cells selected from one of the cell types including suspension human embryonic kidney 293 cells (HEK293F), mesenchymal stem cells (MSCs), neural stem cells (NSCs), dendritic cells (DCs), cardiosphered-erived cell (CDCs), and chimeric antigen receptor-T cells (CAR-T);
   (b') centrifuging the first supernatant at step (a') at 3,000-10,000×g for 30 minutes to obtain a second supernatant in the upper phase;
   (c') filtering the second supernatant at step (b') by a filter membrane with a pore size of 0.22 μm to obtain a filtered solution containing exosomes;
   (d') treating the filtered solution containing exosomes at step (c') by enzyme at a concentration ranging from 0.2 U/mL to 1 U/mL for 2 hours to obtain the sample containing exosomes; and
   (e') mixing a Phosphate Buffered Saline (PBS) buffer to the filtrate containing enzyme-treated exosomes at step (d') at a ratio of (1-3) parts of the buffer solution to 1 part of filtrate containing enzyme-treated exosomes to obtain the sample containing exosomes;
   wherein filtering the sample containing exosomes by tangential flow filtration (TFF) with the following set parameters: a pore size of 300 kDa, a feed flow rate of 25 mL/minute, and a transmembrane pressure of 0.7 bar-1.0 bar, comprising:
   (i) filtering the sample containing exosomes until the volume of the sample containing exosomes is reduced from 10 to 20 times to obtain a first filtered sample containing exosomes; and
   (ii) diafiltrating the first filtered sample containing exosomes two (02) times to obtain the TFF-filtered sample;
   a first time: mixing the PBS buffer to the first filtered sample containing exosomes at a ratio of 1:1 to obtain a first temporary mixture, then filtering the first temporary mixture until the volume of the first temporary mixture is reduced by 50 percent to obtain a second filtered sample containing exosomes; and
   a second time: mixing the PBS buffer to the second filtered sample containing exosomes at a ratio of 1:1 to obtain a third temporary mixture, then filtering the third temporary mixture until the volume of the third temporary mixture is reduced by 50 percent to obtain the TFF-filtered sample; wherein the TFF-filtered sample having 2% DNA contamination;
   wherein centrifuging the TFF-filtered sample by sucrose cushion centrifugation (SCC) having fixed-angle rotor comprising:
   (a") centrifuging the centrifuge tube containing 8 parts of the TFF-filtered sample at stage (A) and 2 parts of 30% sucrose solution at 100,000-130,000×g for 16 hours at 4° C.; then removing 6-7 parts of the solution from the upper phase of the centrifuge tube, collecting a sucrose fraction containing exosomes in the remaining 3-4 parts at the bottom of the centrifuge tube;
   (b") mixing 6-7 parts the the PBS buffer with the sucrose fraction containing exosomes to obtain a foundation solution; and
   (c") centrifuging the foundation solution at 100,000-130,000×g for 3 hours at 4° C., removing the liquid phase to obtain the SCC-centrifuged sample;

wherein purifying the SCC-centrifuged sample by bind-elute size exclusion chromatography (BE-SEC) comprising:
- (a''') mixing the PBS buffer into the SCC-centrifuged sample at stage (B) to obtain a suspension containing exosomes; and
- (b''') loading the suspension containing exosomes into the chromatography column containing 5 mL of resin beads at a rate of 0.5-1.5 mL/minute, and purifying to obtain the purified exosomes, comprising the following three steps:
  - step 1: recovering a first fraction based on the UV 280 nm peak signal at a recovery rate of 0.5-1.5 mL/minute;
  - step 2: further recovering a second fraction containing 10 mL after the UV 280 nm peak signal at a recovery rate of 0.5-1.5 mL/minute; and
  - step 3: creating the purified exosomes by mixing the first fraction based on the UV 280 nm peak signal and the second fraction containing 10 mL after the UV 280 nm peak signal.

2. The method according to claim 1, wherein at step (b'), centrifuging the first supernatant at 3,000-5,000×g.

3. The method according to claim 1, wherein at step (d') treated with enzyme at a concentration 0.5 U/mL for 2 hours.

* * * * *